US010143380B2

(12) United States Patent
Andersson Engels et al.

(10) Patent No.: US 10,143,380 B2
(45) Date of Patent: Dec. 4, 2018

(54) SYSTEM AND METHOD FOR IMPROVED DIFFUSE LUMINESCENT IMAGING OR TOMOGRAPHY IN SCATTERING MEDIA

(71) Applicant: Lumito AB, Lund (SE)

(72) Inventors: Stefan Andersson Engels, Lund (SE); Can Xu, Lund (SE); Haichun Liu, Lund (SE); Pontus Svenmarker, Umeå (SE)

(73) Assignee: Lumito AB, Lund (SE)

( * ) Notice: Subject to any disclaimer, the term of this patent is extended or adjusted under 35 U.S.C. 154(b) by 913 days.

(21) Appl. No.: 14/412,198

(22) PCT Filed: Jul. 1, 2013

(86) PCT No.: PCT/EP2013/063878
§ 371 (c)(1),
(2) Date: Dec. 30, 2014

(87) PCT Pub. No.: WO2014/006012
PCT Pub. Date: Jan. 9, 2014

(65) Prior Publication Data
US 2015/0196201 A1   Jul. 16, 2015

Related U.S. Application Data

(60) Provisional application No. 61/666,899, filed on Jul. 1, 2012, provisional application No. 61/771,131, filed on Mar. 1, 2013.

(51) Int. Cl.
*A61B 5/00* (2006.01)
*G01N 21/47* (2006.01)
*G01N 21/64* (2006.01)

(52) U.S. Cl.
CPC ....... *A61B 5/0071* (2013.01); *G01N 21/4795* (2013.01); *G01N 21/6428* (2013.01);
(Continued)

(58) Field of Classification Search
CPC .......... G01N 21/4795; G01N 21/6428; G01N 21/6456; A61B 5/0071; A61B 5/0073
See application file for complete search history.

(56) References Cited

U.S. PATENT DOCUMENTS 9,012,869 B2 * 4/2015 Andersson-Engels ...................... A61B 5/0059
250/459.1

FOREIGN PATENT DOCUMENTS

WO   WO 2010/128090 A1   11/2010

OTHER PUBLICATIONS

Alerstam et al., White Monte Carlo for time-resolved photon migration, J. Biomed. Opt., vol. 13 (4), pp. 041304-1-041304-10, Jul. 9, 2008.

(Continued)

*Primary Examiner* — David Porta
*Assistant Examiner* — Faye Boosalis
(74) *Attorney, Agent, or Firm* — Knobbe, Martens, Olson & Bear, LLP

(57) ABSTRACT

A method and system for luminescence molecular imaging or tomography of a region of interest in a scattering medium is disclosed. The system comprises a non-linear luminescent marker material arranged in the scattering medium, one or more light sources positioned by at least one light source position for exciting said luminescent marker by excitation light emitted by said one or more light sources into an excitation volume, a detector at a luminescent light detection position detecting luminescence from said luminescent marker due to said excitation light, wherein said excitation light comprises pulsed excitation light.

32 Claims, 17 Drawing Sheets

(52) U.S. Cl.
CPC ........ *G01N 21/6456* (2013.01); *A61B 5/0073* (2013.01); *G01N 2021/6439* (2013.01)

(56) References Cited

OTHER PUBLICATIONS

Culver et al., Optimization of optode arrangements for diffuse optical tomography: A singular-value analysis, Opt. Lett., vol. 26, No. 10, pp. 701-703, May 15, 2001.

Gainer et al., Control of Green and Red Upconversion in Nayf4: Yb3+,Er3+ Nanoparticles by Excitation Modulation, Journal of Materials Chemistry, vol. 21, No. 46, pp. 18530-18533, XP55122657, ISSN: 0959-9428, DOI: 10.1039/C1JM13684D, Jan. 1, 2011.

Gainer, et al.; Toward the Use of Two-Color Emission Control in Upconverting NaYF4:Er3+,Yb3+ Nanoparticles for Biomedical Imaging, Nanoscale Imaging, Sensing, and Actuation for Biomedical Applications VIII, Proceedings of SPIE, vol. 8231, pp. 823101-1-823101-8, Feb. 1, 2012.

Gao, In Vivo Cancer Targeting and Imaging with Semiconductor Quantum Dots, Nature Biotechnology, vol. 22, No. 8, pp. 969-976, 2004.

International Preliminary Report on Patentability dated Sep. 19, 2014 for PCT Application No. PCT/EP2013/063878, filed on Jul. 1, 2013.

International Search Report and Written Opinion dated Sep. 5, 2013 for PCT Application No. PCT/EP2013/063878, filed on Jul. 1, 2013.

Liu, et al.; Multibeam Fluorescence Diffuse Optical Tomography Using Upconverting Nanoparticles, Optics Letters, vol. 35, No. 5, pp. 718-720, Mar. 1, 2010.

Maestro, et al.; Nanoparticles for Highly Efficient Multiphoton Fluorescence Bioimaging, Optics Express, vol. 18, No. 23, pp. 23544-23553, Nov. 8, 2010.

Xu, et al., Fluorescence diffuse optical tomography using upconverting nanoparticles, Applied Physics Letters, vol. 94(3), 251107, Jun. 23, 2009.

Xu, et al.; High-Resolution Fluorescence Diffuse Optical Tomography Developed with Nonlinear Upconverting Nanoparticles, ACS Nano, vol. 6, No. 6, pp. 4788-4795, May 8, 2012.

Yi, et al., Synthesis, Characterization, and Biological Application of Size-Controlled Nanocrystalline $NaYF_4$:Yb,Er Infrared-To-Visible Up-Conversion Phosphors, Nano Letters, vol. 4, No. 11, pp. 2191-2196, Oct. 16, 2004.

\* cited by examiner

Fig. 5a-c

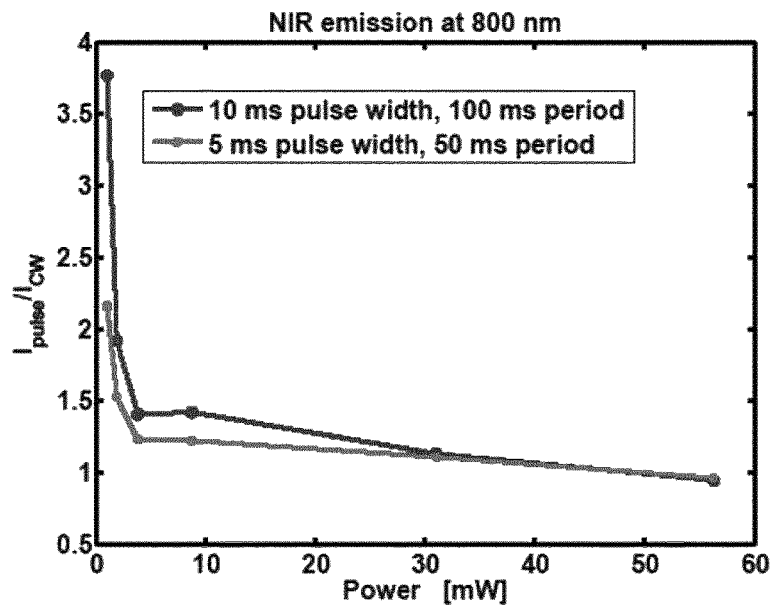
Fig. 14
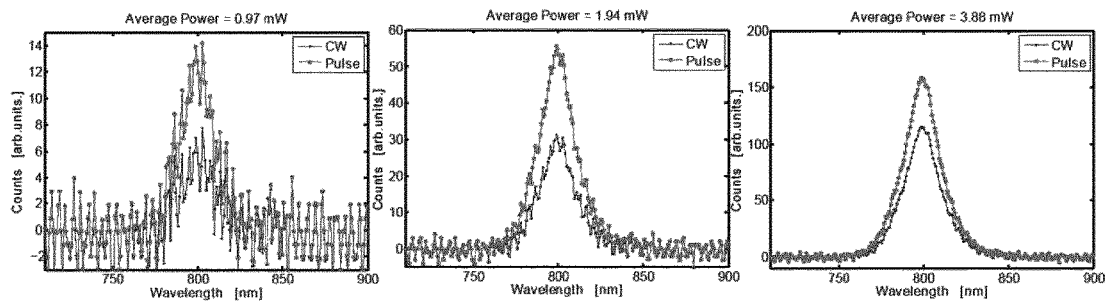
Fig. 15a  Fig. 15b  Fig. 15c
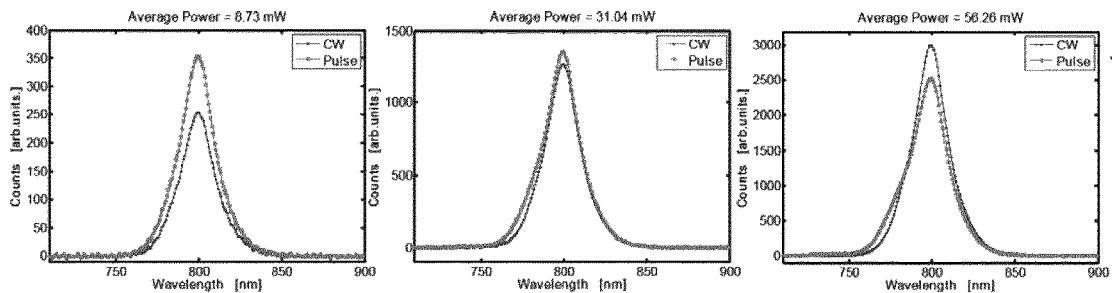
Fig. 15d  Fig. 15e  Fig. 15f

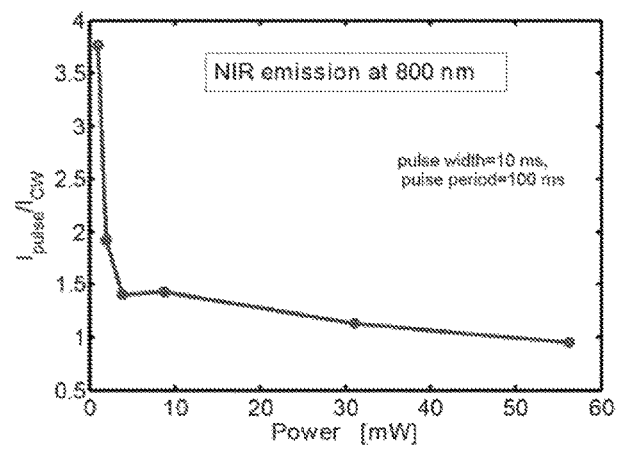
Fig. 16
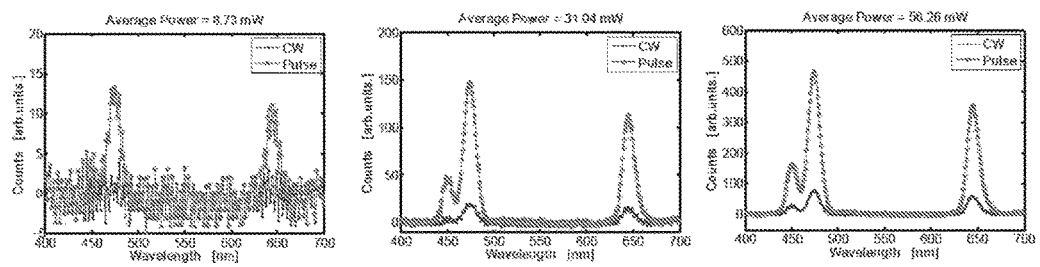
Fig. 17a  Fig. 17b  Fig. 17c
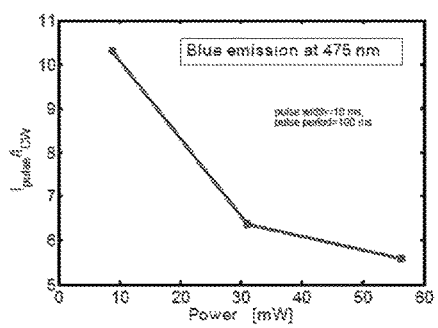 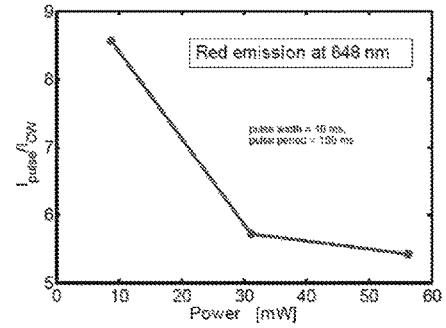
Fig. 18a  Fig. 18b

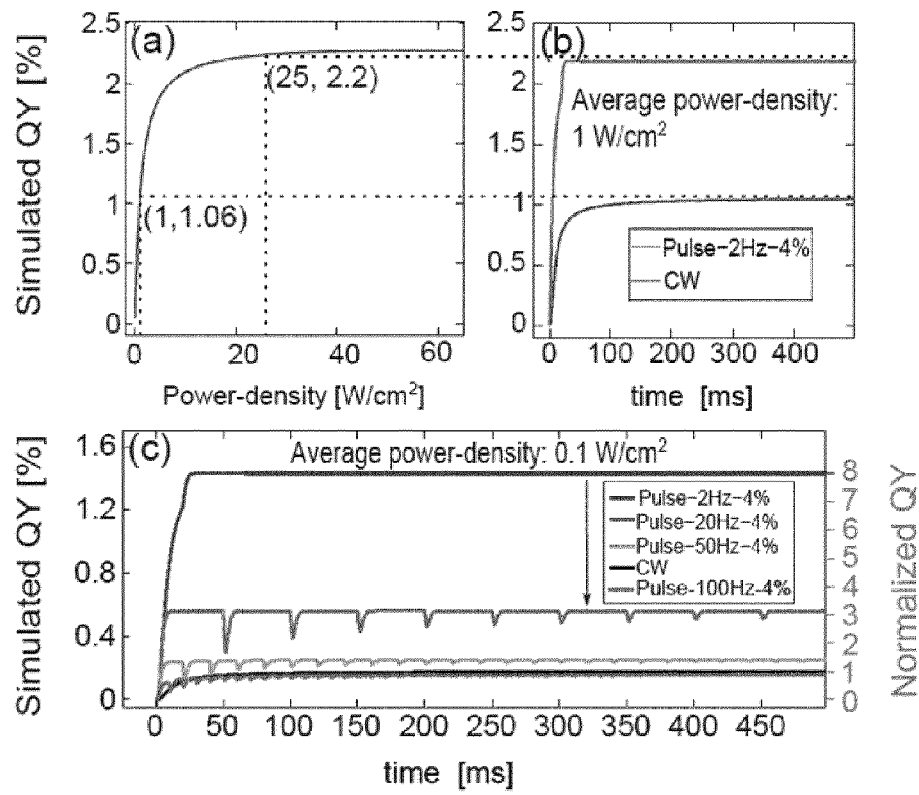
Fig. 29a-c
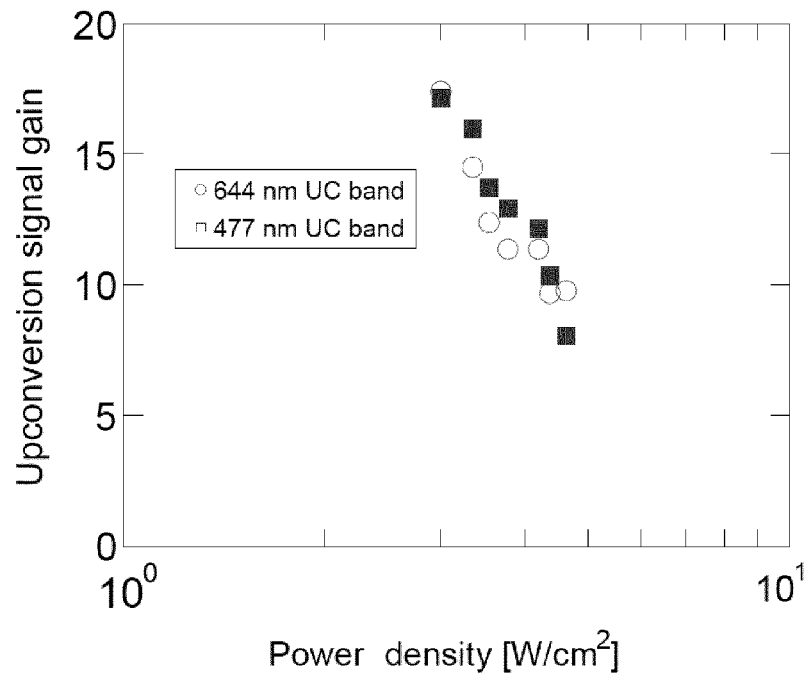
Fig. 30

SYSTEM AND METHOD FOR IMPROVED DIFFUSE LUMINESCENT IMAGING OR TOMOGRAPHY IN SCATTERING MEDIA

FIELD OF THE INVENTION

This invention pertains in general to the field of photoluminescence imaging or photoluminescence tomography of absorbing and scattering media, and in particular to a method and system for such imaging.

BACKGROUND OF THE INVENTION

An example of a scattering medium which is of interest for photoluminescence imaging (in short luminescence imaging) or photoluminescence tomography (in short luminescence tomography) is biological tissue. Tissue optics is a field devoted to study the interaction of light with such tissue. Over the last decades, the field has grown rapidly. With increasing knowledge of the light-tissue interaction, the interest in applying tissue optics as a diagnostic tool is also emerging, reaping the fruits from the fundamental research.

An area in tissue optics, which the present disclosure is partly dealing with, is photoluminescence imaging including photoluminescence tomography, which are non-invasive approaches for in-vivo imaging of humans or animals. These imaging approaches are luminescence-based and require an external source of light for excitation of luminescent biological markers.

Photoluminescence is a process in which a substance absorbs photons and then re-radiates photons. A specific form of luminescence is fluorescence, where typically emitted photons are of lower energy than those used for illumination. Thus, in fluorescence, the fluorescent wavelength is Stokes shifted to a longer wavelength with reference to the wavelength of the illuminating light.

Fluorescent imaging is known and can, for example, be used to study biological responses from drugs in small animals over a period of time, without the need to sacrifice them.

Shimomura, Chalfie and Tsien were rewarded with the Nobel prize in 2008 for discovering and developing the green fluorescent protein, which has become a very important fluorescent marker.

However, hitherto, fluorescence molecular imaging and tomography systems for diffuse luminescent imaging or tomography in absorbing and scattering media suffer from a number of drawbacks. They have for instance a low resolution or contrast, which makes diagnostic tasks based on the imaging results difficult.

Further problems with previous techniques are low quantum yield, shallow imaging depths, long data acquisition times, and thermal side effects.

Thus, there is a need for an improved diffuse luminescent imaging or luminescent tomography system and method which in particular allow for increased effectiveness by improving the aforementioned drawbacks.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a system, a method, and uses according to the appended patent claims.

According to a first aspect of the invention, a method of imaging a region in a scattering medium by diffuse luminescence molecular imaging is provided. The region comprises at least one luminescent marker arranged in the scattering medium at a marker position, where the luminescent marker is a non-linear luminescent marker. The method comprises exciting the luminescent marker by excitation light emitted by one or more light sources into an excitation volume from at least one light source position, detecting luminescence from the luminescent marker due to the excitation light by a detector at a luminescent light detection position, wherein the excitation light comprises pulsed excitation light.

According to a second aspect of the invention, a system for diffuse luminescence molecular imaging of a region of interest in a scattering medium is provided. The system comprises a luminescent marker for use in the luminescent molecular imaging of the scattering medium, where the luminescent marker is a non-linear luminescent marker arranged in the scattering medium. The system comprises one or more light sources positioned by at least one light source position for exciting the luminescent marker by excitation light emitted by the one or more light sources into an excitation volume. The system comprises a detector at a luminescent light detection position detecting luminescence from the luminescent marker due to the excitation light, wherein the excitation light comprises pulsed excitation light.

In embodiments the luminescent marker is comprised in a group of non-linear luminescent markers configured to upconvert incoming light of an illumination wavelength, such that luminescence occurs at a luminescence wavelength that is shorter than said illumination wavelength when said luminescent marker is illuminated with said incoming light.

The luminescent marker is in certain embodiments a biological luminescent marker.

According to another aspect of the invention, a use of a system of the second aspect of the invention is provided for luminescence imaging or tomography of tablets and/or for diffuse optical imaging, and/or photodynamic therapy, and/or remote activation of biomolecules in deep tissues, and/or single-shot deep tissue imaging, and/or for in-vivo or in-vitro luminescence imaging or luminescent tomography of a small animal, and/or for functional diagnostics, such as cancer diagnostics, by said luminescence imaging or luminescent tomography, and/or superresolution microscopy comprising stimulated emission depletion (STED) or single-molecule detection using said non-linear luminescent marker as probe.

In an embodiment, the non-linear markers are attached to an imaging contrast agent for another imaging modality. For instance a non-linear marker is attached to a contrast agent for imaging with a conventional imaging modality, such as Magnetic Resonance Imaging (MRI), X-Ray, etc. In a specific embodiment, a non-linear marker is attached to an organic gadolinium complex or gadolinium compound, which has paramagnetic properties.

Further embodiments of the invention are defined in the dependent claims, wherein features for the second and subsequent aspects of the invention are as for the first aspect mutatis mutandis.

Some embodiments provide for increased emission intensity.

Some embodiments provide for increased resolution in diffuse luminescence molecular imaging and in fluorescence molecular tomography.

Some embodiments provide for determination of distribution of ingredients in tablets. For instance, a non-linear luminescent marker or fluorophore may be attached to an active ingredient in a tablet. The spatial distribution of the active ingredient may thus advantageously be determined.

Some embodiments provide for enhanced contrast in medical magnetic resonance imaging, when non-linear markers are used as an MRI contrast agent. At the same time, luminescence imaging or tomography may be made, providing for functional diagnostic information combined with high resolution MRI of one and the same region of interest and in-vivo.

Some embodiments provide for increased quantum yield when using upconverting nanoparticles.

Some embodiments provide for single-shot deep tissue imaging.

Some embodiments provide for large imaging depths and short data acquisition times.

Some embodiments provide for suppressing of thermal side effects of the excitation light.

Some embodiments provide for diffuse optical imaging, photodynamic therapy and remote activation of biomolecules in deep tissues.

Some embodiments provide for a background-free signal.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 14 shows the gain of signal at 800 nm under pulse excitation with 5 and 10 ms pulse widths under different average excitation power according to an embodiment of the invention;

FIGS. 15$a$-$f$ and FIG. 16 show the influence of excitation power on the gain at 800 nm;

FIGS. 17$a$-$c$ and 18$a$-$b$ show the influence of excitation power on the gain at 800 nm;

FIGS. 29$a$-$c$ illustrates simulated quantum yield (QY) versus time and average power density; and FIG. 30 illustrates the upconversion signal gain versus power density.

DESCRIPTION OF EMBODIMENTS

Figure 1:
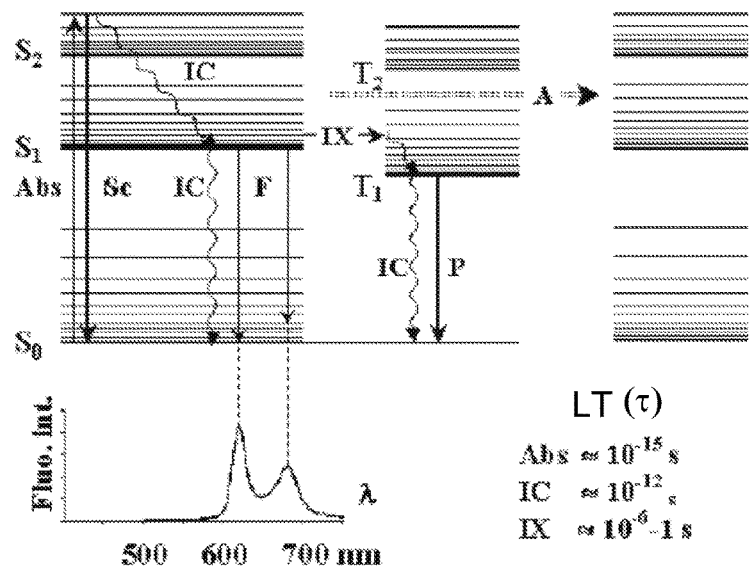
FIG. 1 is a Jablonski diagram.

Some embodiments of this disclosure pertain to an area within the aforementioned tissue optics dealing with diffuse luminescence imaging and tomography. For most visible wavelengths, light does not penetrate more than a few millimeters into tissue. But in the diagnostic window (wavelength 600 to 1600 nm), the light penetration is sufficient to allow imaging through up to several centimeters. This opens up the possibility of imaging fluorescent contrast agents deep in tissue. Previous techniques limit the depth of imaging due to low quantum yield, which also lead to long acquisition times, noise and thermal side effects.

Experiments on tissue phantoms, with realistic optical properties, were performed, and it was shown that it is possible to improve these aforementioned factors according to the below disclosure of the embodiments of the present invention.

It has previously been shown, in WO 2010/128090, which discloses a system, a method, and non-linear luminescent markers for diffuse luminescent imaging or tomography that contrast and resolution of such imaging can be improved.

Several applications within biomedical imaging of the fluorescence imaging or tomography are described below.

Other applications are provided in non-biological areas. Examples for such areas are luminescent imaging or tomography for material testing, including quality control of tablets, filters for liquids or gases through which flows a medium with non-linear markers, etc.

In the context of the present application and embodiment of the invention, fluorescence imaging represents all types of imaging of luminescence. Also, any imaging or tomography discussed is in highly scattering media, traditionally providing poor resolution due to the diffuse character of the light detected. Embodiments of the present invention advantageously improve quantum yield, contrast and resolution of such luminescent imaging, including in luminescent tomography.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Below, an overview of the fundamentals of fluorescence imaging, tissue optics and non-linear markers, such as upconverting nanocrystals are given, followed by a description of results from experiments and simulations. More details are given in WO 2010/128090.

Fluorescence Contrast

The process of light emission from a fluorescing molecule (fluorophore) can be described in a Jablonski diagram, see FIG. 1. FIG. 1 shows a Jablonski diagram showing the various decay paths from an excited state of a molecule. In the lower part of the figure, a fluorescence spectrum from haematoporphyrin in ethanol is shown. The abbreviations are: Sn: singlet states; Tn: triplet states; Abs: absorption; Sc: scattering; IC: internal conversion; F: fluorescence; IX: intersystem crossing; P: phosphorescence; A: transfer to other molecules. Also the approximate time-scale for some processes is shown down right in FIG. 1, as lifetimes (LT), also denoted $\tau$.

If an incoming photon has an energy that corresponds to the gap between two energy bands in the molecule, it can be absorbed. The photon energy will thereby be used for excitation of the molecule to the higher energy band. Excited states are unstable and the molecule will return to the ground state. The deexcitation may follow a number of different pathways, as illustrated in FIG. 1. The labeled levels are electronic levels, corresponding to the energy levels of atoms. S0, S1, etc. are singlet states for which the sum of the electron spin quantum numbers is zero, while T0, T1, etc. are triplet states for which the spin of one electron has changed sign. For large molecules the intervals between the levels are very small and the states overlap due to molecular interactions. When a photon is absorbed by a molecule it will not necessarily excite the molecule to the lowest vibrational level in the excited electronic level, but more likely to a higher vibrational state. This is a result of the Franck-Condon principle stating that during the rapid ($10^{-15}$ s) absorption process, the atoms do not change their location in the vibrational motion. When a molecule is excited to a high energy level, a rapid relaxation to the lowest rotational-vibrational state of S1 will follow. The short time scale ($10^{-12}$ s) of this relaxation is due to the high density of rotational vibrational levels. From S1 the molecules can proceed to the state S0 through radiationless kinetic interactions. This is called internal conversion (IC).

Alternatively, the de-excitation may result in the emission of a photon and this process is called fluorescence. Since the transition may be terminated in any of the rotational-vibrational states of S0, the energy of the different photons will not have a distinct value, but rather a broad distribution. Thus, a fluorescence spectrum from a molecule will be broad, most often without any significant structures. The form of the spectrum will reflect the probability of transitions to the lower levels (S0). In the lower part of FIG. 1 the fluorescence spectrum of haematoporphyrin, which is a tumour marker, or photosensitizer, and will be discussed later on, is shown. Once the pathway absorption-IC-fluorescence is completed, the molecule is back in its original state and configuration. Hence, the fluorescence process is non-destructive and reversible, which is an advantage in, for instance, medical diagnostics.

Several other paths are possible for the excited molecule, such as energy transfer to other molecules, electron transfer, excimer formation and excitation to repulsive states leading to molecular dissociation. These processes are indicated with an A in FIG. 1.

Many fluorescent molecules have one important feature in common, that is the unbroken chain of conjugated double bonds, i.e. every second bond is a double bond. The structure of haematoporphyrin is an example for this (not shown). This is a fluorescent molecule used for fluorescence diagnostics and photodynamic therapy of tumours.

Fluorescence Imaging

Figure 4:
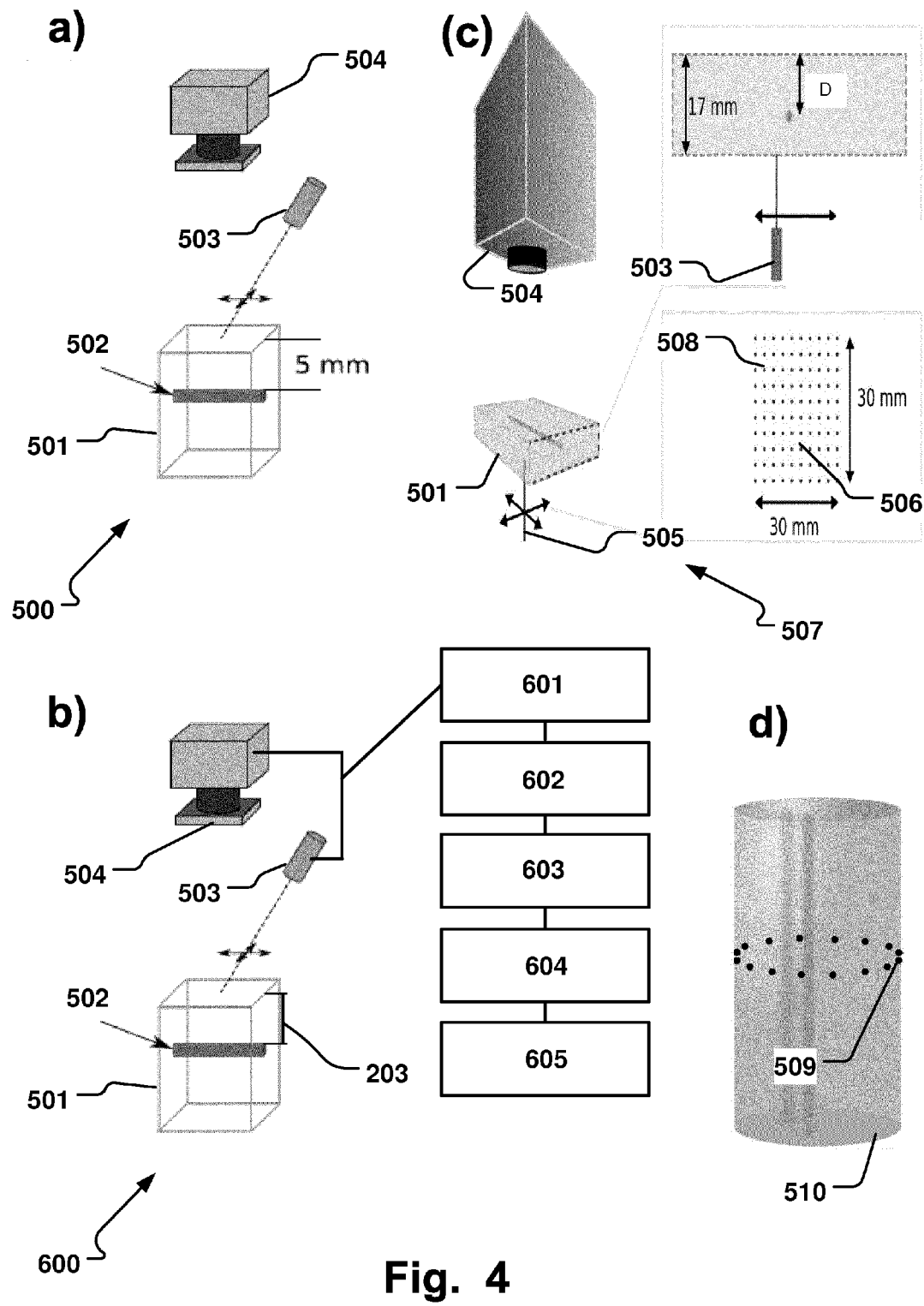
FIGS. 4$a$-$d$ are schematic illustrations of planar imaging implementations, namely ($a$)-($b$) setup used for fluorophore imaging (epi-fluorescence); ($d$) a setup to be used for fluorophore reconstruction in transillumination; and ($c$) another setup for fluorescence diffuse optical tomography.

In contrast to point monitoring devices, Fluorescence imaging systems can detect a fluorescence signal in large number of points. Thus, a two-dimensional image of an area of interest is created. A typical system comprises a camera together with a tunable filter, see FIG. 4a. A similar setup in transillumination is schematically illustrated in FIG. 4c. With a tunable filter the wanted detection wavelengths can easily be selected and a spectral resolution of approximately 20 nm wide may be achieved.

Fluorescence Imaging with Non-Linear Fluorophores

A particularly interesting subsection of fluorescence imaging is that of using non-linear fluorophores. In the context of the present application, a "non-linear marker" is a luminescent marker, wherein a luminescence (L) of the marker is not linearly dependent on the luminous flow of excitation light (E). Non-linear markers thus have a luminescence according to: $L=k*E^x$, wherein $x>1$, and wherein k is a positive constant. The non-linear markers may also have a luminescence according to the following relationships: $L=k*E^x+b$, $L=k(E)*E^x+b$, $L=k(E)*E^x+b(E)$, or $L=k*E^x+b(E)$, where k and b are material constants that are either constant or depending on the local field of excitation light (E), i.e. for k(E) and b(E). In comparison to conventional luminescence imaging, non-linear markers (or fluorophores) may thus require more than one photon for excitation. This drastically decreases the excitation volume and provides a more localized excitation point. In this manner, contrast and resolution of luminescent imaging is improved, as is demonstrated below. In more detail, contrast and resolution of diffuse light in luminescent imaging of absorbing and scattering media is improved. Embodiments of the present invention take advantage of this effect.

To illustrate the difference between fluorescence imaging with linear and non-linear fluorophores, reference is made to FIG. 5a-c. FIG. 5a illustrates a linear fluorescence image in gray-scale. Each pixel (705) corresponds to one excitation point (704) in a grid pattern (701). FIG. 5b illustrates an image obtained with a two-photon, non-linear fluorophore, i.e. non-linear luminescent marker (702). In FIG. 5c the fluorophore (702) is shown in red (larger circle) (703), and the black dots (704) indicate the points of excitation in the grid pattern (701). The circle (703) corresponds to the projected image of the marker (702) on the grid pattern (701). The excitation points (704) corresponds to the positions of the light source, i.e. laser (503), when scanning the luminescent marker (702). It can clearly be seen that using the non-linear fluorophore increases contrast and resolution of the fluorescent image. In particular, when the light source is in the position marked as 706 in FIG. 5c, close to the marker (702) or corresponding projected image (703) of the marker (702) on the grid pattern (701), the excitation volume is sufficiently small and localized to the light source position (706) for the non-linear marker, such that no luminescence is detected in the corresponding pixel (708) in FIG. 5b. For the linear fluorescence image in FIG. 5a, the corresponding pixel (707) receives luminescence due to the increased excitation volume in the scattering media. The two-photon non-linear dependence provides the narrow photon-density of the excitation volume. Thus, imaging the marker (702) based on the non-linear dependence of the detected luminescence on the excitation light intensity, the resolution may be increased.

Non-linear fluorophores require in general higher excitation intensities compared to linear fluorophores and some non-linear fluorophores even require coherent excitation. In scattering media, high intensities are difficult to achieve, since light cannot be focused, but rather spreads in every direction. This makes some non-linear fluorophores more suitable for fluorescence imaging in scattering media as compared to others. The fluorophores need to have an exceptionally high yield, and they may not require coherent excitation. Up-converting nanoparticles are one such non-linear fluorophore with high yield and non-coherent excitation.

Due to the quadratic dependence of the emitted fluorescence in e.g. up-converting nanocrystals, the fluorescence tomography is improved.

Upconversion

Upconversion is a non-linear process that occurs when two or more photons are absorbed and a photon of higher energy, than those of the incoming photons, is released.

The process is for instance observed in materials containing a meta-stable state that can trap one electron for a long time, increasing the interaction-probability with another arriving photon.

In some embodiments, luminescent markers in form of solids doped with different rare earth ions are used to obtain upconversion.

Upconversion can happen due to numerous processes, which impact the upconversion process differently depending on the ion pairs and the excitation intensities.

Figure 2:
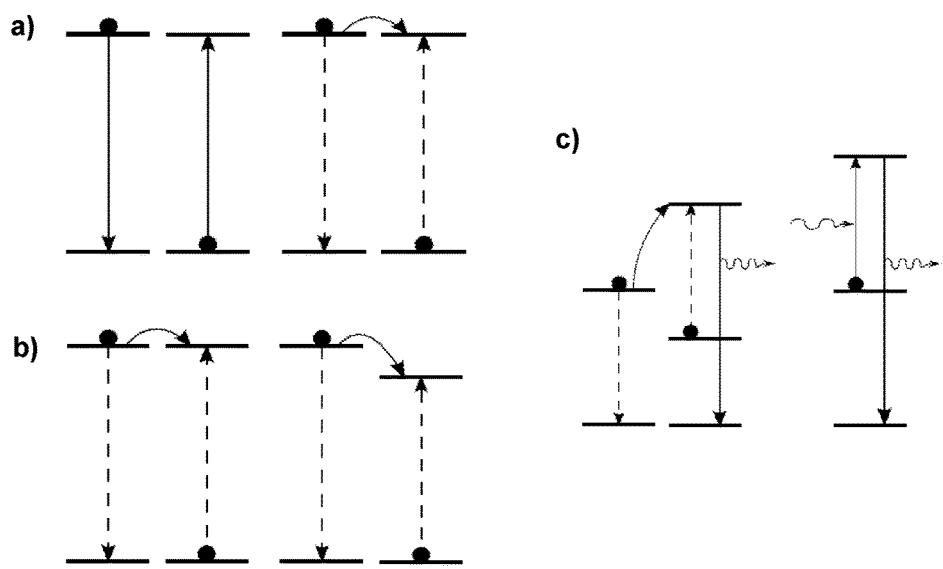
FIGS. 2 $a$)-$c$) are schematic illustrations of $a$) radiative and nonradiative energy transfer; $b$) Resonant and nonresonant energy transfer; and $c$) Comparison of ETU (left) and ESA (right) upconversion.

Some upconversion processes are illustrated in FIGS. 2 a)-c).

Some of the processes involve energy transfer between ions. This energy diffusion, can be radiative or non-radiative, resonant or non-resonant.

Furthermore, Energy Transfer Upconversion (ETU) and Excited-State Absorption (ESA) processes are illustrated in FIG. 2c on the left respectively on the right of the Figure. Excited state absorptions happen when an ion, being in an excited state, absorbs one more photon.

Nanosized Upconverting Crystals

Nanosized upconverting particles are for instance lanthanide doped oxides ($Y_2O_3$), which are easy to fabricate.

Other nanosized upconverting particles are for instance fluorides, which have higher efficiencies than $Y_2O_3$. The higher efficiencies can be explained by the low phonon energies in fluorides, which lower the probability for non-radiative decay.

Further nanosized upconverting particles are for instance made of sodium yttrium tetrafluoride ($NaYF_4$), co-doped with either $Yb^{3+}/Er^{3+}$ or $Yb^{3+}/Tm^{3+}$.

$NaYF_4$ can crystallize in two phases, cubic or hexagonal, called $\alpha$-NaYF4 and $\beta$-NaYF4, respectively. The upconverted luminescence from the $\beta$-phase material is approximately one order of magnitude higher compared to the upconverted luminescence from the $\alpha$-phase. The non-linear fluorophores, such as the upconverting nanoparticles may also be biofunctionalized, giving them, for example, tumor seeking abilities.

The non-linear fluorophores may be water soluble, allowing for easy administration in certain applications, such as in solutions for intravenous, peroral, or enteral administration.

A way to provide upconverting nanoparticles as water soluble, is to coat the particles with a structure that is polar. Coatings may for instance be made of polymers or silica. Both synthetic polymers, for example, Polyethylene glycol (PEG), and natural polymers may be used for the coating. These polymers are stable in biological environments and do not interfere with the optical properties of the nanocrystals in any significant negative way.

Water soluble upconverting nanoparticles may be provided without coatings. Hydroxyl groups may be attached to the surfaces of the upconverting nanoparticles, either by chemical bonds or physical absorption. Hydroxyl groups are by definition formed by covalent binding, and the final structure has polar properties.

Functionalization

Functionalization of the upconverting nanoparticles may be made in similar ways as functionalizing quantum dots, such as described in X. Gao et. al., In vivo cancer targeting and imaging with semiconductor quantum dots, Nature Biotechnology, 22, 8:969-976, 2004, which is incorporated herein in its entirety for all purposes. In Gao et. al. methods are described that are applicable on upconverting rare-earth doped nanoparticles.

Figure 3A:
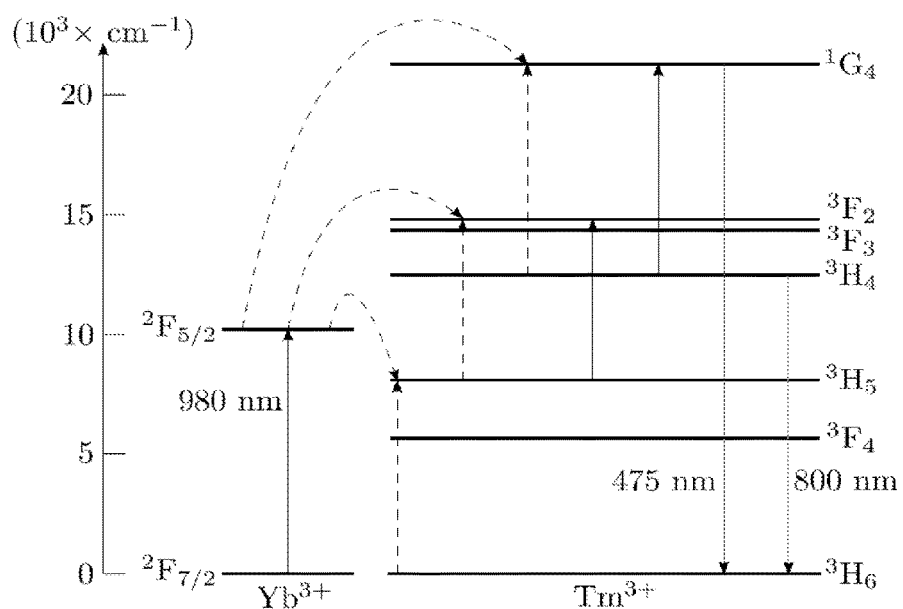
FIG. 3A is a schematic illustration of an upconversion processes in the $Yb^{3+}$—$Tm^{3+}$ ion pair of a upconversion nanocrystal.
Figure 3B:
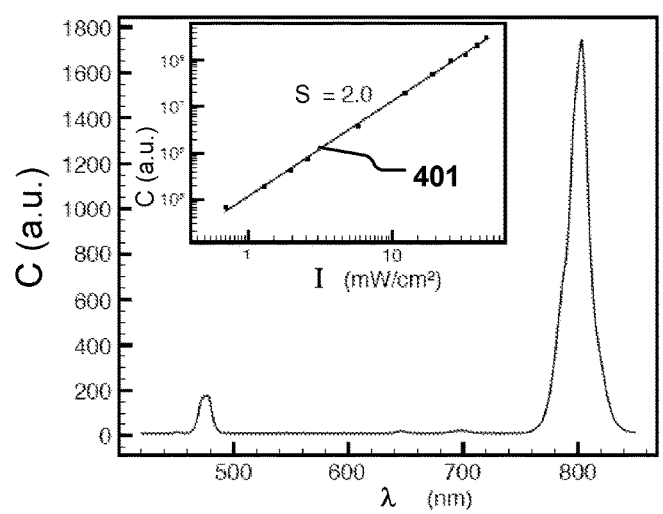
FIG. 3B is a graph showing the emission spectrum for the upconversion nanocrystals of FIG. 3A and the excitation power density dependence of the upconversion emission.

The upconverting nanoparticles used in an embodiment in this disclosure were $NaYF_4$-crystals prepared according to the method described in G. Yi et. al., Synthesis, characterization, and biological application of size-controlled nanocrystalline $NaYF_4$:Yb,Er infrared-to-visible up-conversion phosphors. Nano Letters, 4, 11:2191-2196, 2004, doped with a combination of $Yb^{3+}$ and $Tm^{3+}$. The energy diagrams for the two ions are shown in FIG. 3A. FIG. 3A is a schematic illustration of upconversion processes in the Yb3+/Tm3+ ion pair. Nonradiative upconverting processes are illustrated with dashed arrows and non-radiative decays are omitted for clarity. FIG. 3B is a graph showing the emission spectrum for these upconverting nanoparticles. The blue emission line at 477 nm is only visible for higher pump intensities. The pump-power dependence of the 800 nm line was measured to be quadratic using low intensities, as seen in the inset of FIG. 3B, showing intensity (I) on the x-axis and counts (C) on the y-axis and where the slope (S) of the fitted line (401) equals 2.

In an embodiment, the non-linear markers are attached to an imaging contrast agent for another imaging modality. For instance a non-linear marker is attached to a contrast agent for imaging with a conventional imaging modality, such as Magnetic Resonance Imaging (MRI), X-Ray, etc. In a specific embodiment, a non-linear marker is attached to an organic gadolinium complex or gadolinium compound, which has paramagnetic properties. When used as an MRI contrast agent, contrast is enhanced in medical magnetic resonance imaging. At the same time, luminescence imaging or tomography may be made, providing for functional diagnostic information combined with high resolution MRI of one and the same region of interest and in-vivo.

Other applications are provided in non-biological areas. Examples for such areas are luminescent imaging or tomography for material testing, including quality control of tablets, filters for liquids or gases through which flows a medium with non-linear markers, etc.

System Setup Examples

Systems for diffuse luminescence molecular imaging are shown schematically in FIGS. 4*a-d*. FIGS. 4*a-b* are schematic illustrations of setups for fluorophore imaging (epi-fluorescence); and FIG. 4*c* is a setup for fluorophore reconstruction in transillumination which and can be used for simulations of FMT using non-linear fluorophores and traditional fluorophores. In the latter case the simulated tissue phantom may be modeled as a semi-infinite cylinder (510) having uniformly spaced source-detector points (509) around one plane of the geometry.

A tissue phantom (501) may consist of a solution of intralipid ink with optical properties determined by a suitable system (500, 600), such as time-of-flight spectroscopy system, frequency domain system, or other imaging system in the steady state and time or frequency domain The fluorophores (502) may be contained in capillary tubes with inner diameters of 2.4 mm. The concentrations of the fluorophores may be chosen 1 wt % for the nanoparticles and 1 µM for traditional downconverting fluorophores of the type DY-781 in comparative studies. The concentration of the nanoparticles can be chosen to have a reasonable correspondence with studies using quantum dots, namely a concentration of 1 wt %.

Figure 5:
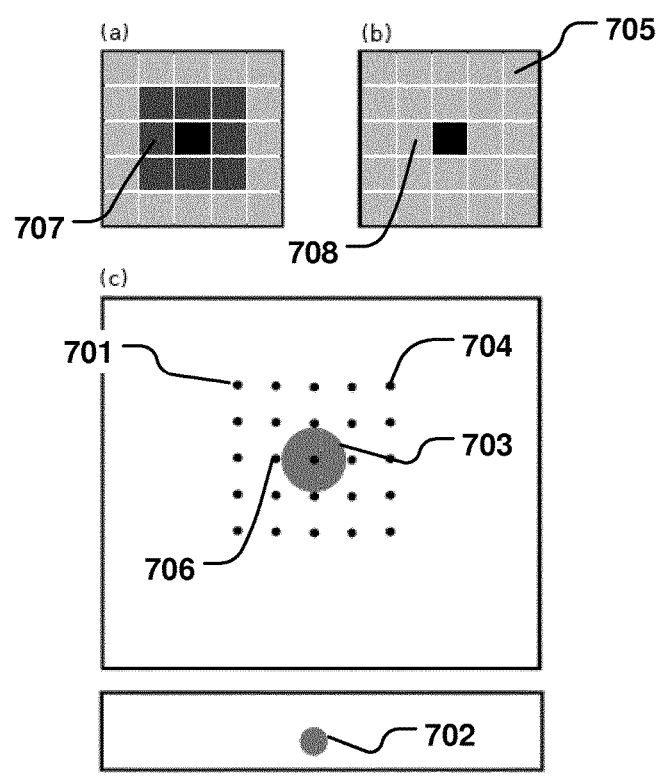
FIGS. 5$a$-$c$ are schematic illustrations of the difference between fluorescence imaging with linear and non-linear fluorophores.

Using step motors, a fiber coupled laser (503) may be raster scanned. The positions of the laser in the raster scan may be described by a grid pattern (701) as shown in FIG. 5. An image may be acquired for each scanned position with an air cooled CCD (504) camera sitting behind two dielectric band pass filters centered at 800 nm. FIG. 4*c* shows a raster scanning setup (507) where the laser is scanning the tissue phantom (501) from a below position (505). The CCD (504) may capture one image for every position (506) of the laser. The positions (506) describes a grid pattern (508) similar to the grid pattern (701) in FIG. 5. For each position (506) of the laser, the emitted fluorescence from the entire side of the phantom (501), i.e. the total luminescence intensity, may be measured and summed to make up one pixel in the resulting image. Hence the number of pixels in the image may be given by the number of excitation positions (506) and not by the number of CCD pixels. The resolution may thus be determined by the photon-density of the excitation light from the laser light source (505), and not by the photon-density of the fluorescence emission light. In this way, because the two-photon photon-density in the excitation volume is more narrow than the single-photon photon-density, the resolution could be increased. When summing the total luminescence intensity a threshold value may be applied to the detected luminescence. In this way resolution may be increased. For example, only if the luminescence intensity is above a defined threshold it will be added to the total luminescence intensity. The threshold may be defined as a value in the CCD (504), for example if the luminescence intensity is below 30% of a peak value it will be discarded, as it might be considered as a background signal. Further, if the resulting total luminescence for a pixel, or position (506) of the laser, is below another threshold value it may be considered as background signal and removed. Alternatively, the quadratic intensities of the luminescence signal may be summed. In this way the resolution may be further increased. For example, the luminescence intensity detected by the CCD (504), which may have relative value between 0 and 1 by definition of a peak intensity value in the CCD, may be multiplied with itself before added to the total luminescence intensity for the current pixel or position (506). Further, the total luminescence intensity may be multiplied with itself for each pixel or position (506). Using the scanning imaging technique, each pixel in the image may correspond to the fluorescence induced by a single excitation point, i.e. light source position (506).

FIG. 4*b* schematically illustrates a system 600 for diffuse luminescence molecular imaging according to an embodiment of the invention. The system 600 comprises a luminescent marker 502 for use in said luminescent molecular imaging of said scattering medium, wherein the luminescent marker is a non-linear luminescent marker arranged in the scattering medium. The system 600 comprises further one or more light sources 503 positioned by at least one light source position 505, 506, for exciting the luminescent marker by excitation light emitted by said one or more light sources into an excitation volume, and a detector 504 at a luminescent light detection position detecting luminescence from the luminescent marker due to said excitation light, wherein said excitation light comprises pulsed excitation light. Hence, the system 600 is adapted for diffuse luminescence molecular imaging of a region of interest in a scattering medium by pulsed excitation light, which provides for improved quantum yield, less thermal side effects due to less heating of the medium, deeper imaging depths and shorter acquisition times. The system 600 will be described further in the below disclosure in relation to enhancing upconversion emission by pulse excitation and single pulse imaging with pulsed excitation light.

Multi-Beam Fluorescence Diffuse Optical Tomography Using Upconverting Nanoparticles Additionally, this disclosure demonstrate a method in Fluorescence diffuse optical tomography to exploit the unique nonlinear power dependence of upconverting nanoparticles to further increase the amount of information in a raster-scanning setup by including excitation with two beams simultaneously. It was found that the increased information led to more accurate reconstructions.

Fluorescence diffuse optical tomography (FDOT) is a relatively new modality which seeks to reconstruct the spatial distribution of the concentration of fluorescent probes inside turbid material. As an imaging tool, it has a good prospect in biomedical studies to image, for example, tumors, proteases, and drug effects.

FDOT has numerically very ill-posed issues. In this issue, the quality of the reconstructions for the fluorescent target is directly determined by the amount and quality of fluorescence information obtained from boundary measurements. Instrumental noise and tissue autofluorescence are the main perturbations of the measurements, resulting in poor signal quality, and can cause severe artifacts in the reconstructed results. In order to overcome this, one could, for example, employ low-noise equipment, use background subtraction or spectral unmixing. However, such methods cannot resolve all issues, since they essentially are only utilizing the present information in a better way rather than adding new constraints for the reconstructions, i.e., adding new independent information, which is critical to improve the quality of the reconstructions.

In a noncontact CCD-based FDOT system, one preferred way to gain more information is by increasing the number of excitation positions. However, in order to keep the intensity of the excitation beam within reasonable levels, there is a limit on the minimum size of the excitation beam. This implies a practical upper limit to the highest excitation-position density, since distinct, i.e., non-overlapping, excitation positions are desired for reconstructions. It is also possible to employ an anatomical imaging modality such as magnetic-resonance imaging to provide a-priori structural information. However, this is at the cost of significantly increased complexity and reduced flexibility of the system.

In this disclosure, we present an approach to exploit the quadratic power dependence of upconverting nanoparticles to gain additional information by utilizing two beams simultaneously for excitation in FDOT. The effect of the images taken with dual-beam excitation (named type-D images) on the reconstructions of the nanoparticle number density distribution, n, is demonstrated. In addition, comparisons of reconstructed results between the linear Rhodamine 6G and the quadratic upconverting nanoparticles are made.

The excitation and emission fields can be modeled by two coupled diffusion equations [Ref. 1]. For quadratic fluorophores, the fluorescence signal detected at a fixed detector position under excitation of the k:th beam can be described by the forward model (1);

$$\Gamma_k = \sum_{i=1}^{N} U_f^*(r_d, r_i) n(r_i) [U_e(r_{s_k}, r_i)]^2 \Delta V_i, \quad (1)$$

where N denotes the number of voxels,
$r_{s,d,i}$ denotes the coordinates for source, detector, and voxel, respectively, and;
$\Delta V_i$ is the volume of voxel i.
The forward solution of the excitation light is represented by;
$[U_e(r_{s_k}, r_i)]^2$
When exciting the medium using two beams simultaneously, the detected signal is given by (2);

$$T_{k\&j} = \sum_{i=1}^{N} U_f^*(r_d, r_i) n(r_i) [U_e(r_{s_k}, r_i) + U_e(r_{s_j}, r_i)]^2 \Delta V_i \quad (2)$$

$$= \Gamma_k + \Gamma_j + 2 \sum_{i=1}^{N} U_f^*(r_d, r_i) n(r_i) U_e(r_{s_k}, r_i) U_e(r_{s_j}, r_i) \Delta V_i,$$

which reveals the involvement of cross-terms. In a raster-scanning setup (500, 507), if two images are taken sequentially with one excitation beam scanning over two positions (named type-S images), and a third image is taken with two-beam excitation (type-D) above the previous two positions, the involvement of cross-terms implies that the type-D image cannot be obtained by any mathematical manipulation from the existing type-S images, indicating that it is independent and contains additional information. However, for linear fluorophores, e.g., Rhodamine 6G, the type-D image is only linear combinations of the existing type-S images, and will not add more constraints for the inverse problem. For nonlinear fluorophores, it is deduced that Eq. (2) can be generalized to include more simultaneous excitation beams. The significance of the measurements with dual-beam excitation in the reconstructions was confirmed by the singular-value analysis of the weight matrix, W, whose elements are given by (3) [Ref. 1];

$$W_{(s,d),i} = U_f^*(r_d, r_i)[U_e(r_s, r_i)]^\gamma \Delta V_i, \quad (3)$$

with;
$\gamma=2$ for quadratic fluorophores and;
$\gamma=1$ for linear fluorophores.
Calculations were performed using the NIRFAST package implementing the finite element method. W was factorized according to (4);

$$W = U\Sigma V^*, \quad (4)$$

where U and V are unitary matrices containing the left and right singular vectors of W, and; $\Sigma$
is a diagonal matrix containing the singular values of W. The column-space of V is spanned by the image-space modes, while the column-space of U is spanned by the detection-space modes. The singular values of W denote how effectively a given image-space mode can be detected by an experimental setup [Ref. 2].

Figure 6:
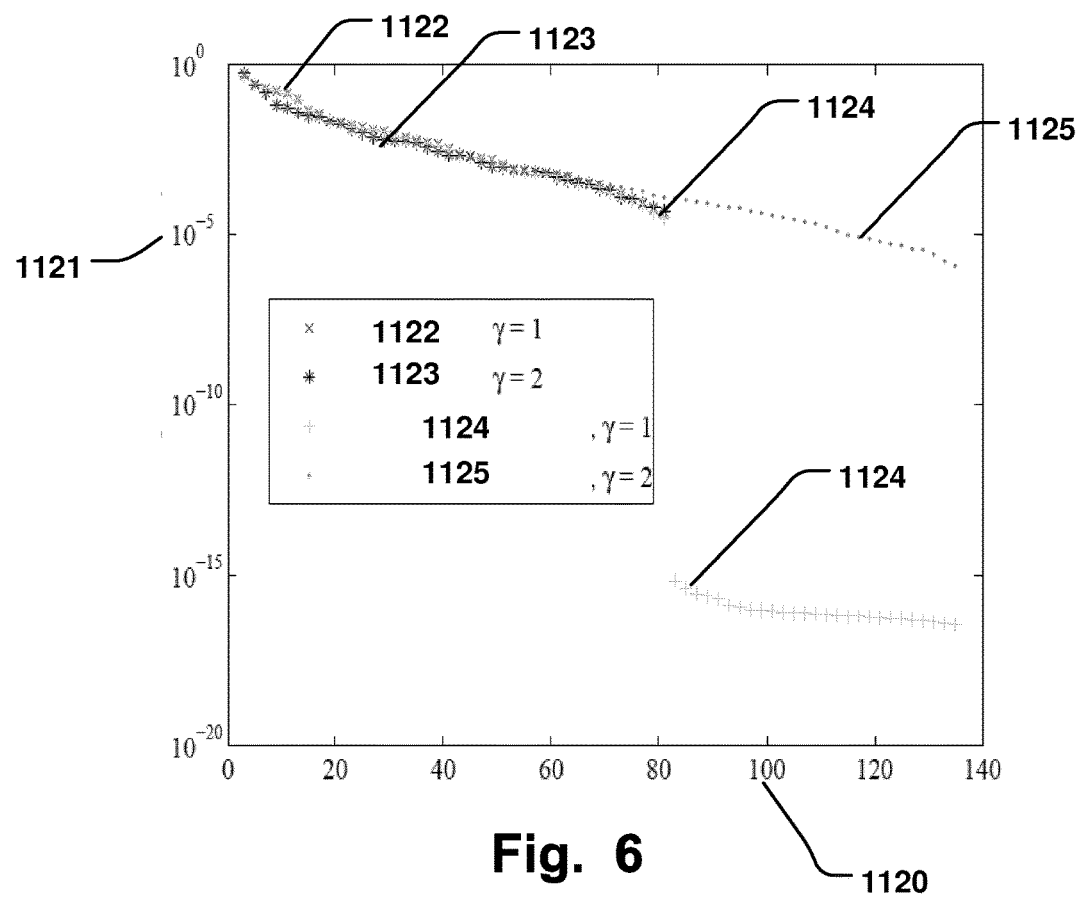
FIG. 6 is a graph showing the normalized singular-value distribution of a weight matrix W, for single-beam excitation and combined single-beam excitation and dual-beam excitation.

FIG. 6 shows the normalized singular-value distribution of W. The x-axis shows the singular value index (1120) and the y-axis shows the normalized singular value intensity (1121). For clarity, only every second singular value are shown. The cross (1122) and plus (1124) signs represent the linear fluorophore ($\gamma=1$), the former for the single-beam excitation (1122), while the latter for the combined single-beam excitation and dual-beam excitation (1124). As seen, the normalized intensities of the additional singular values due to dual-beam excitation (1124) have dropped to machine precision, which indicates that the measurements with dual-beam excitation may not alleviate the ill-posedness of FDOT. In other words, the type-D images may not provide more information than the existing type-S images. Hence, it may not improve the quality of the reconstructions. However, for the quadratic fluorophore (denoted by asterisk (1123) and dot (1125) signs in FIG. 6, the intensities of the additional singular values (1125) are still significant. This implies that type-D images will contribute to the quality of the reconstructions.

A single excitation beam may first be used to scan over a (3×3) grid, and capturing one image for each scanned position by a CCD camera. In the next step, two excitation beams, located at two nearest-neighboring sites of the same grid, can be simultaneously employed to illuminate the phantom, giving 6 extra type-D images.

Figures 7A, 7B:
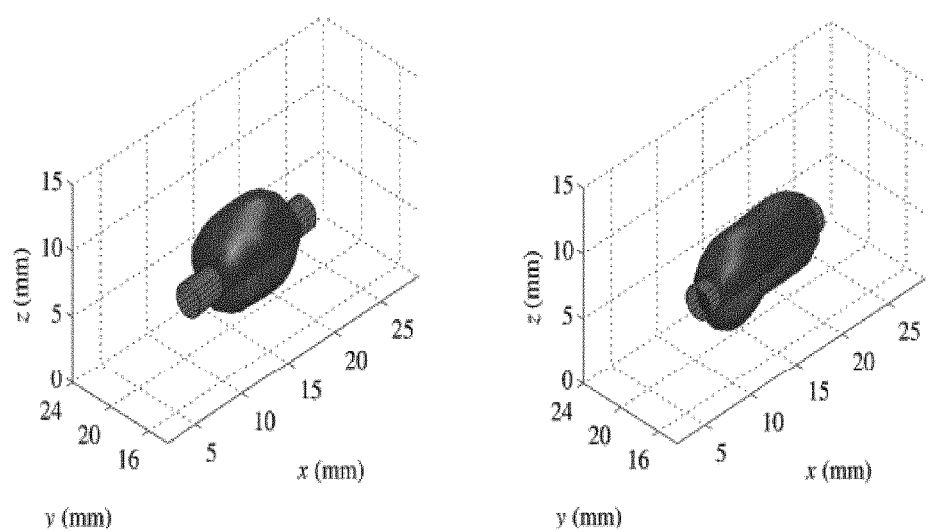
FIGS. 7A-B are three-dimensional reconstructions of upconverting nanoparticles, using (10A) only single-beam images, and using (10B) both single-beam and dual-beam images.

FIGS. 7A-7B shows the three-dimensional rendering of the reconstructed upconverting nanoparticles. The red cylinders in the subfigures are identical and represent the true fluorescent lesions. In the reconstruction of FIG. 7A, only type-S images were used. As can be seen, the shape of the fluorescent lesion is overestimated. This overestimation may be explained by the ill-posedness of the inverse problem.

When adding type-D images, the reconstruction of the fluorescent lesion shape is improved remarkably, as shown in FIG. 7B. Images of type D contribute to the inverse problem and lead to better reconstructions for the quadratic upconverting nanoparticles.

It is disclosed an additional unique advantage of the nonlinear power dependence of upconverting nanoparticles. This advantage enables the possibility to obtain additional information for the inverse problem by using images taken with two or more excitation beams simultaneously. The same advantage could not be found when using linear fluorophores, e.g., Rhodamine 6G.

Enhancing Upconversion Emission by Pulsed Excitation

Figure 8:
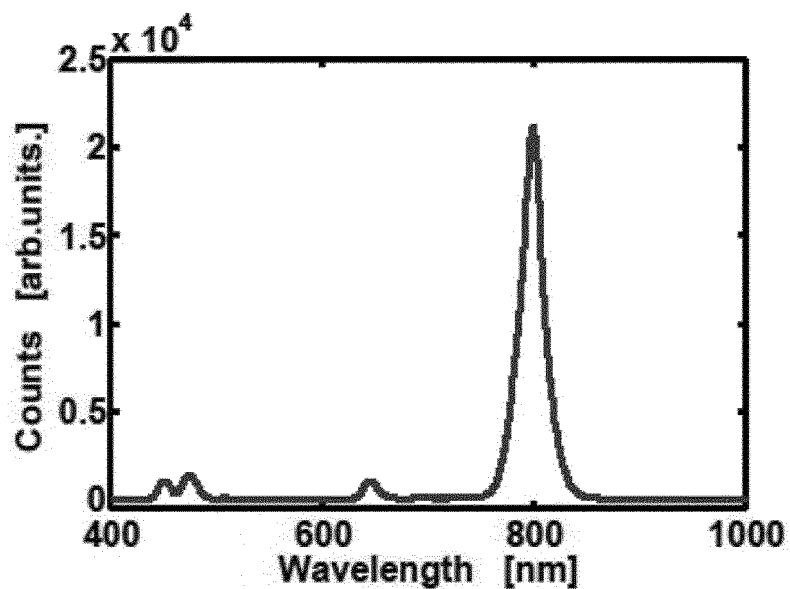
FIG. 8 shows upconversion spectrum of NaYF4:Yb3+, Tm3+ nanoparticles under excitation of 975 nm.

As shown in FIG. 8, illustrating upconversion spectrum for NaYF4:Yb3+, Tm3+, upconverting nanoparticles can emit emission bands in the near infrared (~800 nm), red (~648 nm) and blue (~475 nm) ranges under excitation of 975 nm.

As described above, the intensities of these upconverting emission bands have nonlinear dependencies on excitation intensity. The dependence in low intensity range can be described by $$I_f = k I_{ex}^n \quad (5)$$

where $I_f$ is the upconversion fluorescence intensity; k is a constant; $I_{ex}$ is the excitation intensity; n is the number of excitation photons required in order to generate one emission photon.

Figure 9:
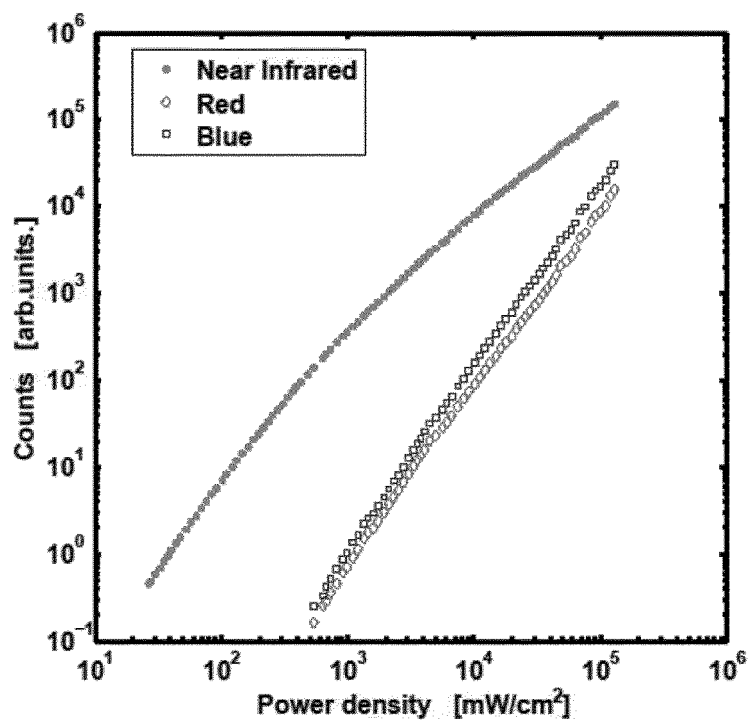
FIG. 9 shows power dependencies of near infrared, red and blue upconversion emission bands of NaYF4:Yb3+, Tm3+ nanoparticles under excitation of 975 nm determined according to an embodiment of the invention.

The power dependencies of the near infrared, red and blue emission bands are shown in FIG. 9, illustrating power dependencies of near infrared, red and blue upconversion emission bands of NaYF4:Yb3+, Tm3+ nanoparticles under excitation of 975 nm.

Figure 10:
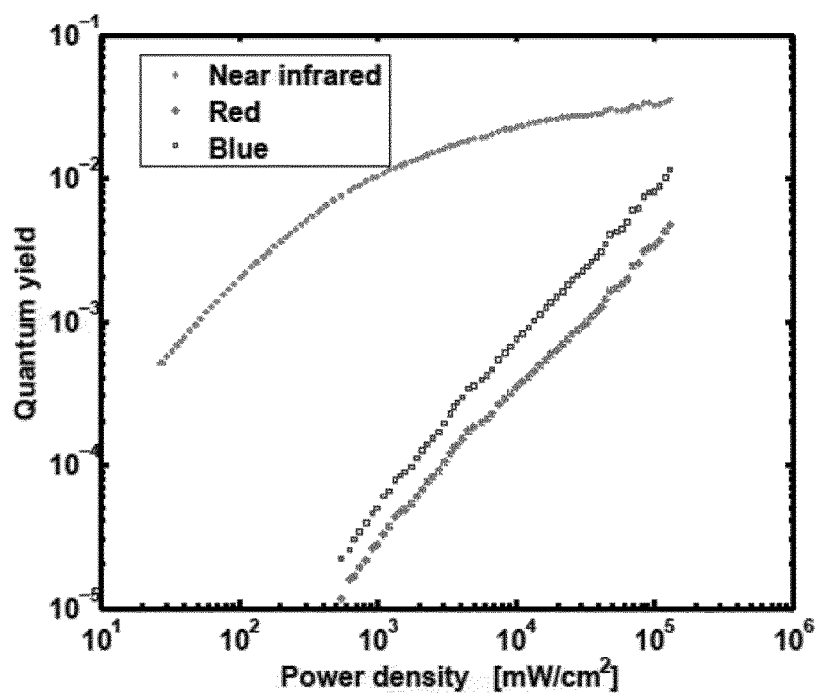
FIG. 10 shows quantum yields of near infrared, blue, red upconversion emission bands at various power densities determined according to an embodiment of the invention.

Quantum yield is defined as the ratio between the numbers of emitted photons and the number of absorbed excitation photons. Because of their nonlinear power dependencies shown in FIG. 9, upconversion emissions have power-density dependent quantum yields instead of constant quantum yields, as illustrated in FIG. 10, showing quantum yields of near infrared, blue, red upconversion emission bands at various power densities.

Figure 28:
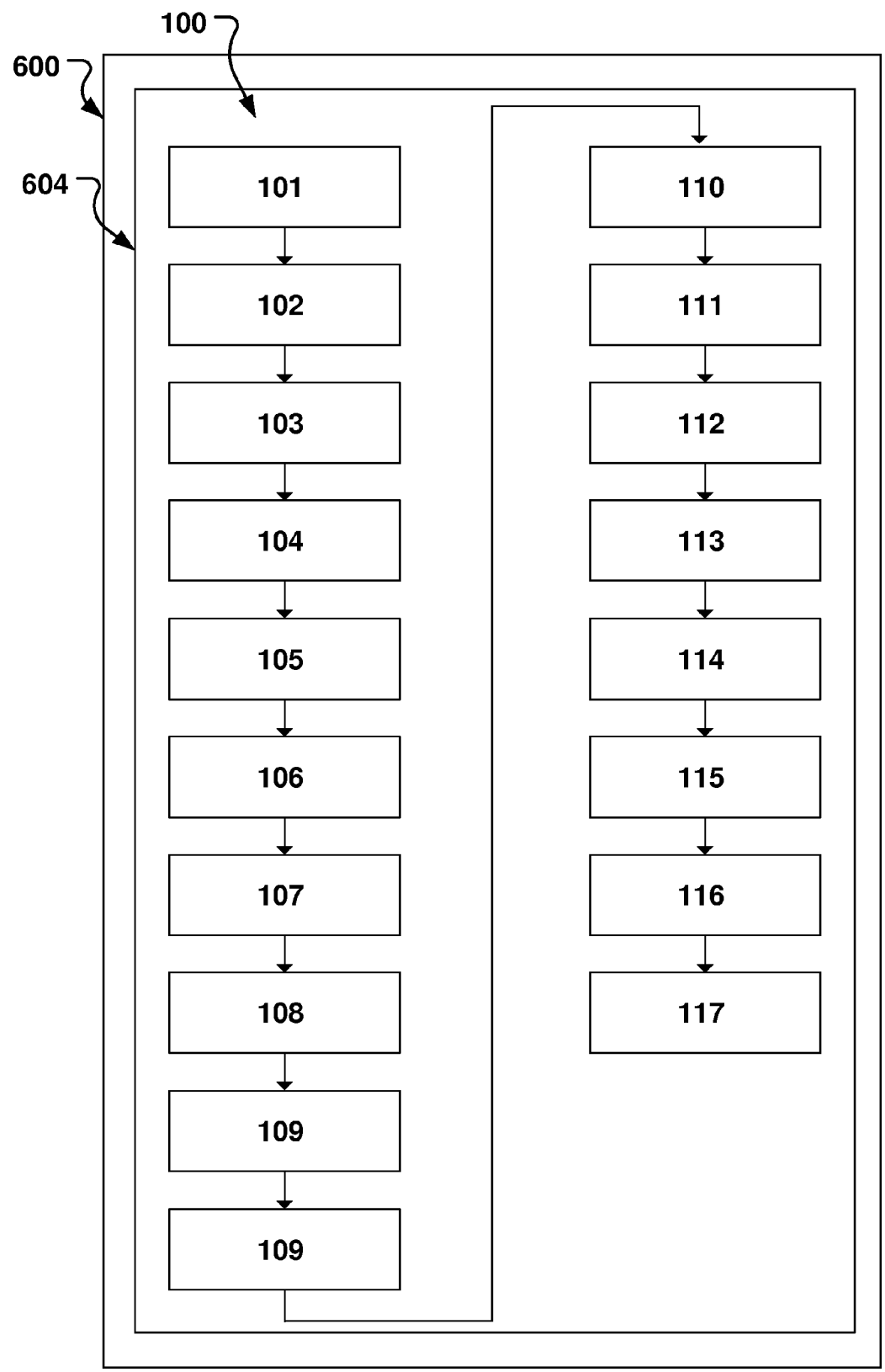
FIG. 28 illustrates a schematic flow-chart of a method according to embodiments of the invention.

A method 100 of imaging a region in a scattering medium by diffuse luminescence molecular imaging according to an embodiment of the invention comprises (FIG. 28) providing 101 at least one non-linear luminescent marker in a scattering medium at a marker position in said region, exciting 103 the non-linear luminescent marker by excitation light emitted by one or more light sources into an excitation volume from at least one light source position, and detecting 107 luminescence from the luminescent marker due to the excitation light by a detector at a luminescent light detection position, wherein the excitation light comprises pulsed excitation light.

The quantum yield increases with power density and gradually approach a constant. A gain in the signal level is provided from pulse excitation compared to continuous wave excitation with the same average power, because the pulse excitation has higher peak power.

Figure 11:
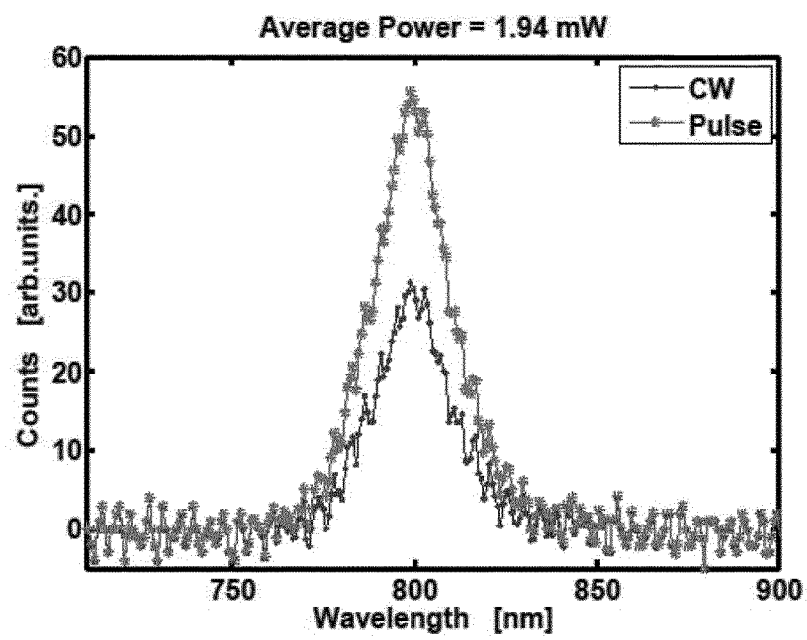
FIG. 11 shows upconversion spectra of NaYF4:Yb3+, Tm3+ nanoparticles under excitation of CW and pulse excitation (with identical average power) according to an embodiment of the invention.

Confining the same number of excitation photons in a narrow time window through pulse excitation can hence be provided for more efficiently using excitation photons in order to get stronger upconversion emission light. This is confirmed in FIG. 11, showing spectra of NaYF4:Yb3+, Tm3+ nanoparticles using CW or pulsed light with the same average power as excitation. The pulse has a pulse width of 10 ms and a period of 100 ms, and the beam sizes both for the CW and pulse excitation is 0.70 mm in diameter in FIG. 11. As shown in FIG. 11, a signal gain by a factor of around 2 is obtained by using the pulse excitation compared with the CW excitation with the same average power of 1.94 mW.

By having pulsed excitation light a significant increase in quantum yield when using upconverting nanoparticles is accordingly provided. Further, pulsed excitation light provides for single-shot deep tissue imaging, large imaging depths and short data acquisition times compared with continuous wave excitation. Thermal side effects of the excitation light are also suppressed because of the pulsed light.

Pulsed excitation light also provides for diffuse optical imaging, photodynamic therapy and remote activation of biomolecules in deep tissues. The aforementioned effects have been described in more detail under "Single shot imaging" below, which is part of the present application.

Figure 21:
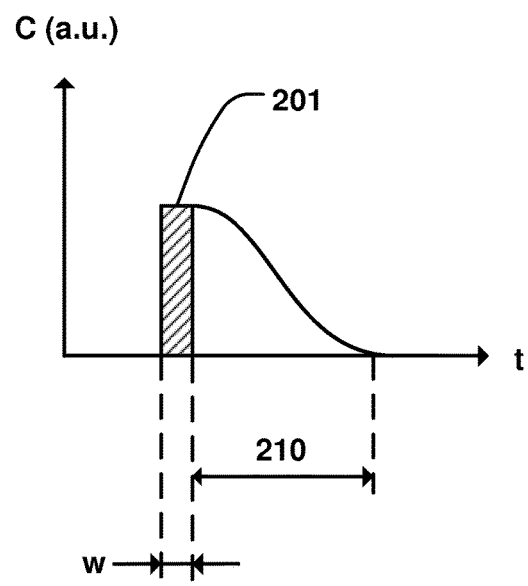
FIG. 21 illustrates luminescence and delayed detection of luminescence following pulsed excitation light according to embodiments of the invention.
Figure 22:
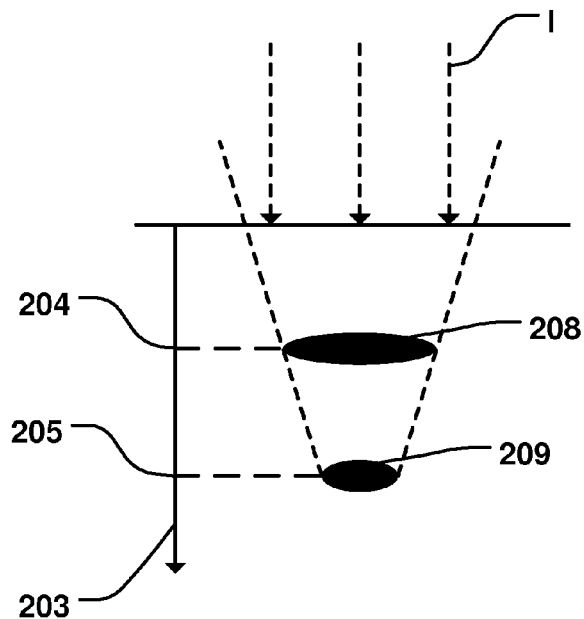
FIGS. 22-25 illustrate relative depth coordinates of markers and the determination thereof according to embodiments of the invention.

An additional advantage with pulsed excitation and UCNPs with long emission lifetime is that it is possible to suppress scattered excitation light by employing delayed detection. This has previously not been utilized for UCNPs. For macroscopic imaging inside tissue a great advantage of the UCNPs is the anti-Stokes shift of the light emission, proving means to suppress the tissue autofluorescence. This is known and provides in theory a total background free signal, of great interest. Even though tissue autofluorescence can be totally suppressed, there is still in practice an issue in prior art with spectrally filtering out the signal from the much stronger scattered excitation light. With pulsed excitation and time-delayed detection, this suppression would be more efficient, and the advantage with total background-free signal would be easier to utilize in practice with pulsed excitation. The method 100 may thus comprise the step of time-delaying 105 the detection of the luminescence to provide for detection of a signal without the influence of the excitation light scattered in the medium. FIG. 21 shows an example where an excitation pulse 201 with length (w) is followed by luminescence with a decaying intensity during a time interval 210. The method may thus comprise the step of detecting 108 the luminescence during the time interval 210 succeeding the pulse 201 of said excitation light. The time interval may be in the range of 1-100 ms. The system 600 may accordingly comprise a detector unit 601 that is operable to detect the luminescence during a time interval 210 succeeding a pulse of said excitation light.

Pulse Width Dependent Gain:

Under CW excitation, if the excitation power is doubled, the fluorescence intensity will be four times higher if the power-densities are in the non-saturation power-density regime, due to the quadratic power dependence (case 1).

Figure 12:
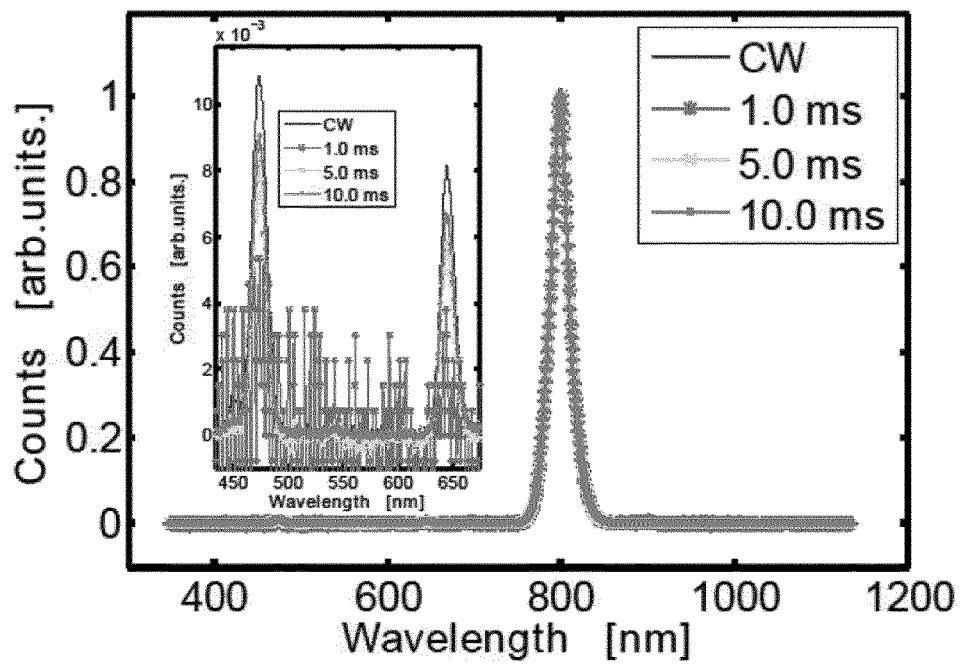
FIG. 12 shows upconversion emission spectra (normalized at 800 nm) under CW excitation and pulse excitation with different pulse width (1 ms, 5 ms, 10 ms) according to an embodiment of the invention.

Under pulsed excitation, it will take a certain time (determined by the lifetimes of intermediate energy levels) to reach steady state. During the rise time, the fluorescence intensity is weaker than that at steady state condition. Thus, comparing the fluorescence intensities under CW excitation and under a square-wave pulse excitation with twofold higher peak power, during the period of pulse duration, the latter will not be fourfold higher but less than the former, which is different from case 1. Hence, the gain in upconversion emission intensity by pulse dexcitation is pulse width dependent. If the pulse width is too short, the upconversion system will be far away from steady state during the pulse duration, thus the gain will be smaller or no gain at all. The pulse width should be long enough, and it can be determined with the assistance of the observation of the upconversion spectra under CW excitation and pulse excitation with different pulse width. If the pulse width is long enough to reach steady state, the normalized spectrum under pulse excitation should adequately approach that under CW excitation. FIG. 12 shows the upconversion emission spectra (normalized at 800 nm) under CW excitation and pulse excitation with different pulse width (1 ms, 5 ms, 10 ms). The CW excitation has an average power of 24 mW (beam size 0.70 mm). The peak powers of all the pulses is 24 mW (beam size 0.70 mm). The inset of FIG. 12 shows the zoomed-in part of the range of 434-674 nm. As seen, when the pulse width is 10 ms, the difference between the spectra from CW and pulse excitation is less than 10%, indicating steady state or quasi steady state is reached.

Figure 13:
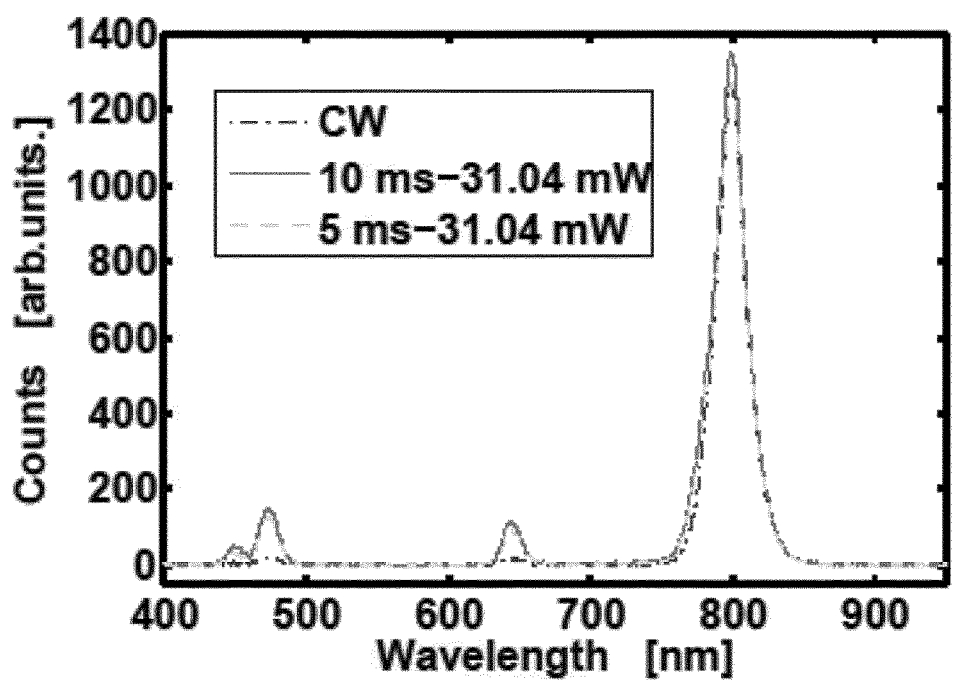
FIG. 13 shows upconversion spectra under excitation of CW and pulses (with the same average power of 31.04 mW) according to an embodiment of the invention.

When the pulse width is increased from 5 ms to 10 ms, the gain is increased, as shown in FIG. 13 (showing upconversion spectra under excitation of CW and pulses with the same average power of 31.04 mW) and FIG. 14 (showing the gain of signal at 800 nm under pulse excitation with 5 and 10 ms pulse widths under different average excitation power).

Power Dependent Gain:

The quantum yield of the emission at 800 nm gradually approaches a constant when increasing the power density, as shown in FIG. 10. Thus, the gain decreases with increasing the average power. When the average power is in the range in which quantum yield is a constant, no gain any more. We even lose some signal due to the quantum yield loss during the rise time above mentioned, as shown in FIGS. 15*a-f*, 16.

Since the blue and red emission have large slopes in the power dependence curves (as shown in FIG. 9), e.g., larger n in equation (5), thus higher order power-density dependent quantum yields than 800 nm emission (as shown in FIG. 10), and they are more difficult to get saturated (as shown in FIG. 9 and FIG. 10), in stark contrast their gain are larger than that of 800 nm. Even at the maximum power investigated, there are still gains by factors of 5.3 and 5.7 for the red and blue emissions, respectively, as shown in FIGS. 17*a-c*, 18*a-b*.

It is noteworthy to point out that the gain by pulse excitation is related with the parameters of the pulse. All the above results are obtained with square wave pulse excitation. Different pulses such as triangle or sine wave will give different results, but signal gain can be also expected. The duty cycle of the square wave is another key parameter, which determines what maximum gain could be obtained. The pulse with a pulse width of 10 ms and period of 100 ms has a duty cycle of 10%, so the maximum gain could be 10 (1/duty cycle) for 800 nm emission. Examples show a gain by a factor of around 3.8. By using smaller duty cycles, larger gain may be shown. Hence, the present disclosure provides for improved gain by using small duty cycles, for example well below 50% duty cycle which would only allow a gain by a factor of 2. By using small duty cycles it is provided for achieving optimally high peak power for improved imaging abilities with the advantages described herein. By using single pulse excitation as explained below even higher power density can be achieved in order to exploit high intrinsic QY of upconversion nanoparticles. The pulsed excitation provides accordingly for delivering high power densities while complying with ANSI standards.

Power-Scanning Tomography

The change of the power dependence shown in FIG. 9 can be used to perform power-scanning tomography using a single excitation point and any number of detection points. The concept can be briefly summarized as a discretization of the power-dependence curve, where at each discretized region, a given slope coefficient is used as input to generate (simulate) the expected fluorescence. This can be further used to perform a tomographic reconstruction using conventional optimization methods in an extremely fast fashion, by only power-scanning the excitation source with no spatial scanning. Advantages include, speed, no-moving parts, and simplified instrumentations.

In conclusion, by using pulse excitation, upconversion emission intensity can be enhanced compared with CW excitation with the same average power. The enhancement originates from the use of the same amount of excitation photons with a higher efficiency, which results from the power-density dependent quantum yield of upconversion nanoparticles, here $NaYF_4$:$Yb^{3+}$,$Tm^{3+}$. The gain is pulse width and power dependent.

This proposed technique is a general approach for utilizing the upconversion capability more efficiently. It will work for not only $Yb^{3+}$/$Tm^{3+}$ codoped upconverting nanoparticles, but also for any upconverting nano- or bulk-materials. It works even better for high order upconversion emission, such as the blue and red emission of $Tm^{3+}$ from three-photon processes. This approach can be useful in enhancing shorter wavelength upconversion emission needed for photodynamic therapy in biological tissue.

The power-dependence feature of upconversion emission can be used to perform power-scanning tomography using a single excitation point.

Upconversion Signal Enhancement by Pulse Excitation in Tissue Phantom

Figure 19A:
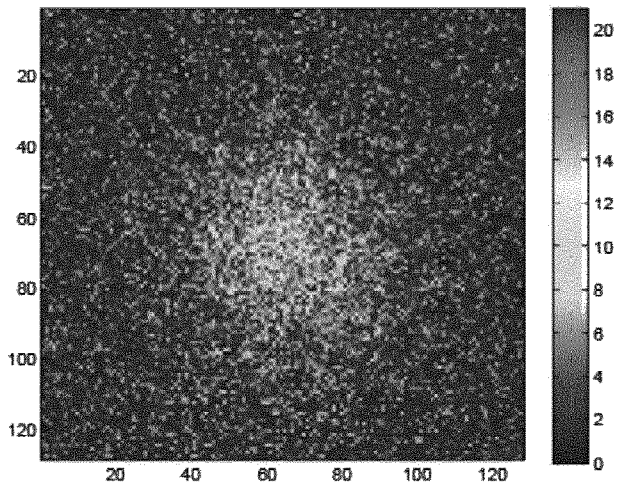
FIG. 19$a$-$c$ show luminescence images taken at 800 nm under the excitation of; a CW laser diode with a power of 100 mW ($a$); a pulse laser (square wave, pulse width 5 ms, period 250 ms) with an average power of 100 mW ($b$); and a pulse laser (square wave, pulse width 10 ms, period 500 ms) with an average power of 100 mW ($c$)
Figure 19B:
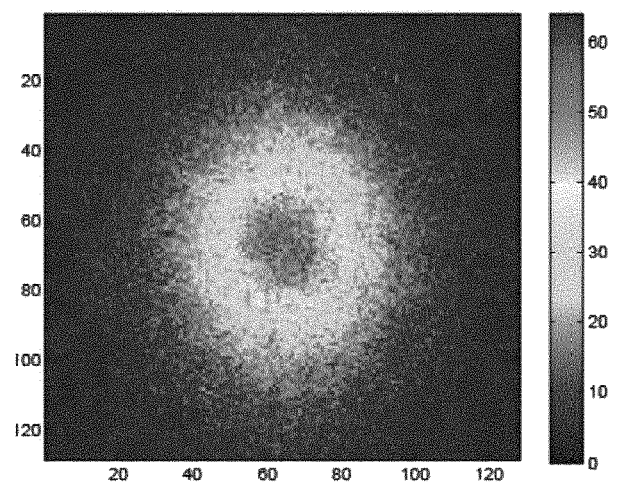
Figure 19C:
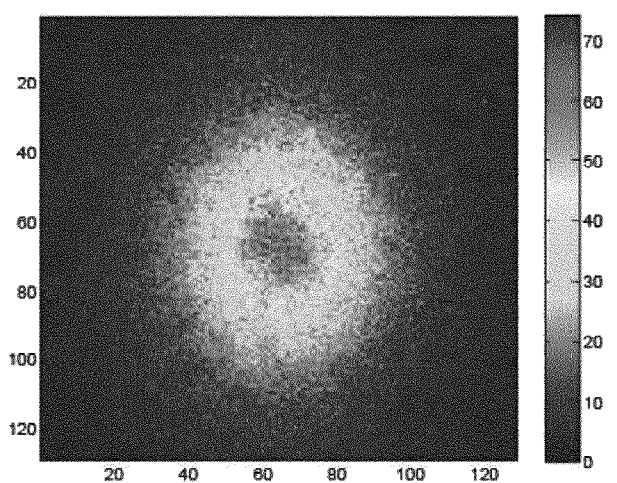

The validity of this technique is also confirmed by measurement in tissue phantom, see FIGS. 19*a-c*. The experiments were carried out in a 20 mm thick liquid tissue phantom with a reduced scattering coefficient of 10 $cm^{-1}$ and an absorption coefficient of 0.5 $cm^{-1}$, made of water, intralipid and ink. A glass tube with inner diameter of 2 mm, filled with hexane colloidal of $NaYF_4$:$Yb^{3+}$,$Tm^{3+}$ nanoparticles (c=1 wt %), was inserted into the phantom with a depth of 10 mm. Two laser sources were used for the comparison, a CW laser diode at 975 nm and a pulse laser with tunable pulse width and period at the same wavelength. The spot sizes of the lasers were 1 mm in diameter. Two different settings were used for the pulse laser: (a) Setting 1: 5 ms pulse width, 250 ms period, FIG. 19*b*; (b) Setting 2: 10 ms pulse width, 500 ms period, FIG. 28*c*. The upconversion emission images taken at 800 nm under the excitation of CW or pulse excitation are shown in FIGS. 19*a-c*. The average power was kept the same (100 mW) for all the measurements. The intensities under pulse excitation is around 6 and 6.75 times higher than that under CW excitation for Setting 1 and 2, respectively.

FIG. 19*a* show an image taken at 800 nm under the excitation of a CW laser diode with a power of 100 mW.

FIG. 19*b* show an image taken at 800 nm under the excitation of a pulse laser (square wave, pulse width 5 ms, period 250 ms) with an average power of 100 mW.

FIG. 19*c* show an image taken at 800 nm under the excitation of a pulse laser (square wave, pulse width 10 ms, period 500 ms) with an average power of 100 mW.

The higher intensities obtained from the pulsed excitation provides for improved imaging due to the increase of the upconversion signal level. Further, the pulsed excitation reduce the heating effects in the biological tissue, while maintaining the increased signal level and improved imaging. For example, a single shot (10 ms-100 ms) by a laser (peak power up to e.g., 100 W) to generate a strong peak signal, and then turning off the excitation source will allow the biological tissue to cool down, in order not to overheat the tissue but dramatically increase the emission signal. Further, it would be possible to use a very low-power light source with pulsed excitation light to achieve acceptable signal levels for the imaging, in comparison to continuous wave laser diode that would require more power to produce the same result.

Single-Shot Imaging with Pulsed Excitation Light

The limited quantum yield (QY) of upconverting nanoparticles (UCNPs), especially at low light conditions, is of major concern for most potential biological applications. Two highly potent techniques in the field are deep tissue optical imaging and photodynamic therapy (PDT), which both require high QY. The present low QY issue hinders the potential of these techniques by resulting into increased treatment and data acquisition times and shallow applicable depths. Although, the low QY can to some extent be overcome by elevating the excitation light level, such improvements are restricted for CW excitation by risks of side-effects in terms of tissue heating (regulated by the ANSI standards). According to embodiments of the invention, by employing pulsed excitation, it is provided for to break through the low power-density limit of upconversion (UC) emission while limiting the thermal effect of the excitation light. In addition, the applicability of UCNPs may be further boosted by utilizing single-shot excitation schemes. Similar to multiphoton microscopy, pulsed excitation may provide high photon density during the pulse, while keeping the average power (meaning the deposited energy responsible for the heating) moderate. Due to the nonlinear power-density dependence of UC emission, pulsed excitation provides for beneficial effects as discussed in this disclosure.

Examples of the present disclosure take excitation dynamics of UC emission into account to overcome issues with previous techniques that demonstrate low quantum yield. The below disclosure gives examples of experiments and simulations demonstrating significant QY increase which can be achieved by using pulsed excitation light in a method, system and use of a system according to embodiments of the invention. E.g. pulsed excitation light is used with matched pulse characteristics, i.e., with sufficiently long pulse width and non-saturated transitions to provide for the advantageous effects. This makes pulsed excitation an ideal excitation approach for UCNPs, especially for deeply located tissue volumes. In addition, single-shot imaging of UCNPs can be implemented due to the increased QY, in which the data acquisition time can be shortened by orders of magnitude while improving the imaging depth as compared to CW light excitation causing the same temperature increase. Thus the present disclosure has the potential to fundamentally broaden the applicability of UCNPs in deep tissue regions relying on diffuse light excitation.

The excitation dynamics can be modelled using rate equations. Without loss of generality, NIR UC emission at 800 nm of $Yb^{3+}/Tm^{3+}$ codoped system may be used as a model in the below example. FIG. 29(a) shows the simulated QY at steady state conditions following CW excitation of different power densities. As seen, the QY increases with the excitation power-density in a complex rather than a purely linear manner, and exhibits a feature of gradual saturation, i.e., approaching a constant at high excitation power-densities. FIG. 29(b) presents the simulated temporally cumulative QY under CW excitation and under pulsed excitation in the first pulse period. The CW excitation has a constant power-density of 1 W/cm2. The pulsed excitation, having a frequency of 2 Hz and a duty cycle of 4%, has power-densities of 25 W/cm2 and 0 W/cm2 at the "on" and "off" states, respectively, thus resulting in the same average power-density as the CW excitation. As seen, under CW excitation, the UC emission has a constant QY except at the very early stage when the energy levels are populated due to transient effects of the excitation. This constant QY is associated with the steady state of the UC system, and given by the QY at the power-density of 1 W/cm2 in FIG. 2(a). Under the pulsed excitation, the QY is very small at the start of the laser pulse, and then increases with time. If the length of pulse duration allows, the QY will surpass the QY under the CW excitation, and asymptotically approach a maximum. This maximum is restricted to the QY at steady state at the power-density of 25 W/cm2 in FIG. 29(a). Clearly, the advantage of using pulsed excitation to replace the equivalent CW excitation is that the late excitation photons can be potentially used with higher energy conversion efficiency, while the cost is that the early excitation photons in each pulse period are used with lower efficiency than in the CW excitation. Through balancing the increased power-density and decreased excitation time under the same amount of energy, an overall UC signal gain can be expected.

Long-term QY in multiple periods under pulsed excitation was investigated, in order to determine the influence of the pulse width on the potential signal gain. The average power-density was kept at 0.1 W/cm2. The pulsed excitation used in this study had the same duty cycle of 4% unless otherwise specified, and its frequency was adjusted in order to achieve different pulse widths. As illustrated in FIG. 29(c), a significant UC signal gain is obtained by using pulsed excitation when the frequency is well below 50 Hz. For example, the signal gain by the 2-Hz square wave in the time interval of [0, 500] ms is approximately 8. The signal gain decreases with frequency, i.e., increases with pulse width. When the frequency is even higher, e.g., up to 100 Hz, the signal generated by the pulsed excitation becomes slightly smaller than that generated by equivalent CW excitation. It should be noted that the signal gain decreases with the applied power-density. When the average power-density is increased to 1 W/cm2, the gain declines to 2. This can be ascribed to the gradual saturation property of UC emission, as indicated in FIG. 29(a).

Figure 26:
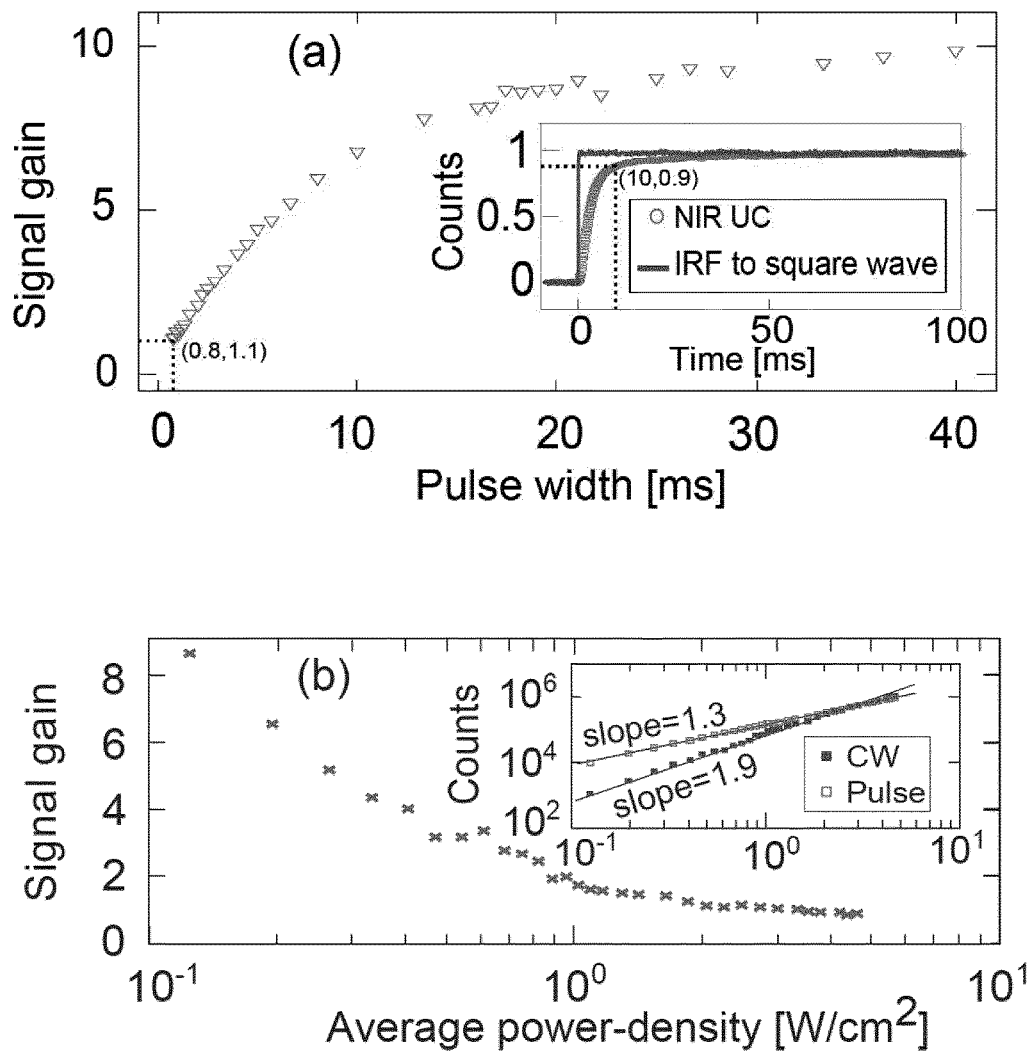
FIGS. 26$a$-$b$ illustrates signal gain versus pulse width and average power density respectively.

In order to experimentally validate the gain in signal due to pulsed excitation as indicated by simulations above, experiments were carried out on colloidal stable stable core-shell $NaYF_4:Yb^{3+},Tm^{3+}@NaYF_4$ UCNPs dispersed in hexane. The prepared UCNPs emit the major UC emission bands at around 800 nm under excitation of 975-nm light, as shown in FIG. 3(b). The intensities of this NIR UC emission under CW excitation and under pulsed excitations with different pulse widths were recorded. The average power-density of the excitation light was kept at 0.12 W/cm2. As shown in FIG. 26(a), a signal gain, monotonically increasing with pulse width, was obtained by using the pulsed excitation even with a pulse duration of 0.8 ms. When the pulse width reaches 20 ms, the gain is as high as 8.7. These results agree well with the simulated results presented in FIG. 29. It is noteworthy to point out that the required pulse width for signal gain in the present case (~0.8 ms) is much shorter than the rise time of the UC emission, approximately 10 ms as shown in the inset of FIG. 26(a).

The dependence of the UC signal gain on the applied power-density was also investigated using a square-wave excitation with a fixed pulse width of 20 ms and a period of 500 ms, together with the equivalent CW excitation. FIG. 26(b) shows the UC signal gain by the pulsed excitation at various average excitation power-densities, where a decreasing trend with increasing excitation power densities is clearly seen. At the minimum power-density investigated (~0.12 W/cm2), the signal gain is approximately 8.6, while at the maximum power-density (~4.65 W/cm2), the UC signal generated by the pulsed excitation is slightly weaker than that generated by the CW excitation. The UC emission intensity dependence on the excitation power-density exhibits a smaller slope than under the CW excitation, as shown in the inset of FIG. 26(b). This can explain the signal-gain trend above. The amplification effect of increasing the excitation power-density here essentially originates from the non-linear power-density dependence of the UC emission. Thus, a higher-order power-density dependence would result in a larger UC signal gain. This is confirmed by the measurements on the blue and red UC emissions, both generated through a three-photon excitation process. They exhibit significantly larger signal gains than the NIR UC emission at any given average power-density, as shown in FIG. 30.

The merit of using pulsed source as the excitation approach to image deeply located UCNPs was subsequently validated in a liquid tissue phantom. The phantom, made of water, intralipid and ink, was determined by a photon time-of-flight spectroscopy (pTOFS) system to have a reduced scattering coefficient of $\mu'_s$=10.1 cm$^{-1}$ and an absorption coefficient of $\mu_a$=0.52 cm$^{-1}$ at 975 nm, and had a thickness of 17 mm. A glass tube with an inner diameter of 2 mm, containing the colloidal core shell UCNPs (c=1 wt %), was inserted into the phantom as the luminescent inclusion to mimic a UCNP-labeled target (e.g., a tumor) inside real tissue. One out of two 975-nm lasers, including a CW laser diode and a pulsed laser with a pulse width of 20 ms and a period of 500 ms, was used to provide the excitation light. The average power-density impinging on the surface of the tissue phantom was 1.2 W/cm2 for both excitation approaches. The excitation source and the detector were positioned in a trans-illumination geometry.

Figure 27:
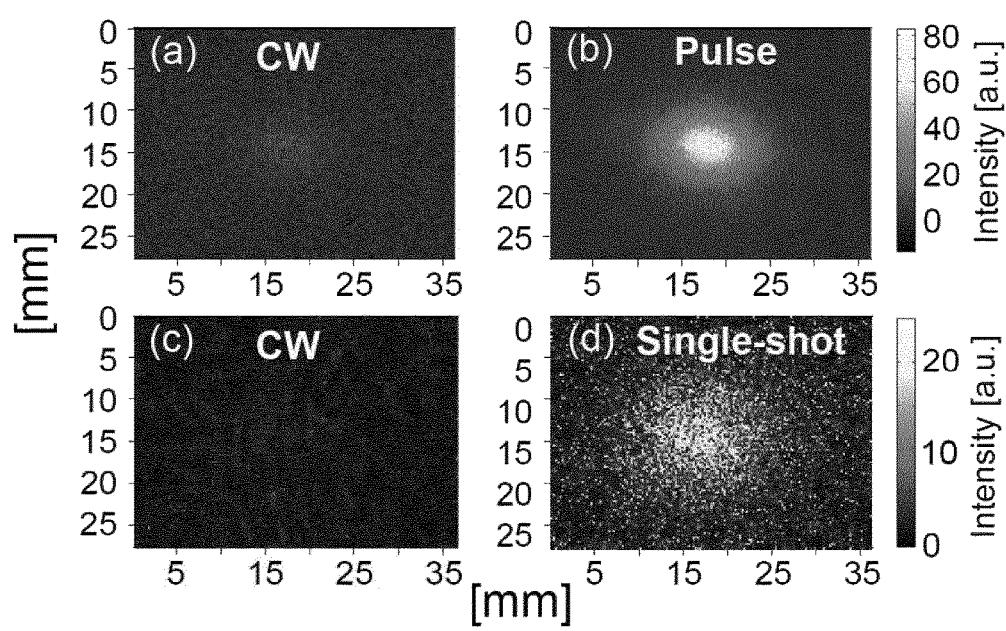
FIGS. 27$a$-$d$ illustrates luminescence from a marker following pulsed excitation according to embodiments of the invention ($b$, $d$) and luminescence from continuous wave (CW) excitation ($a$, $c$)

When buried at a depth of 10 mm from the source, the luminescent inclusion was barely detectable under CW excitation even with an exposure time of 10 s, as shown in FIG. 27(a), whereas by using pulsed excitation, the signal-to-background ratio was significantly increased by a factor of approximately 7 under the same detection conditions, as illustrated in FIG. 27(b). An obvious implication is that the data acquisition time can be remarkably reduced and the imaging depth can be increased if keeping the signal quality as the equivalent CW excitation. The QY of UC emission may be further optimized by using a single pulse as excitation providing even higher power-density. For example, the maximum permissible power-density for exposure to human skin at 975 nm is 17.4 W/cm$^2$ for a repetitive pulse excitation with a pulse width of 20 ms and a frequency of 2 Hz, while the number for a 50-ms single pulse is as high as 36.9 W/cm$^2$, referring to the supplemental material. Such strong single pulse with a pulse width longer than the rise time of the UC emission enables the UCNPs to be used in a very efficient way in terms of energy conversion. This excitation approach would improve the imaging ability of using UCNPs without violating the ANSI standard.

The feasibility of single-shot imaging was thus experimentally investigated. A 50-ms single pulse providing an excitation power-density of 36.9 W/cm$^2$ was used. When the luminescent inclusion was placed at a depth of 13 mm from the source, it could still be relatively well detected using the single pulse excitation with an exposure time of 1 s, even using an epi-fluorescence imaging setup, as shown in FIG. 27(d). Nevertheless, when the CW laser was used as the excitation source, also outputing the maximum permissible powerdensity by ANSI standard on the same illumination area, i.e., 709.6 mW/cm2, the inclusion was not detectable at all even with a much longer exposure time of 10 s, as shown in FIG. 27(c). The exposure time for the single pulse excitation may be shortened to 50 ms still without loss in the UC signal quality, as long as the excitation source and the detector are synchronized. The examples demonstrated here show the great potential of single-shot UCNP excitation in UCNP-guided deep tissue optical imaging.

Single-shot imaging of UCNPs in deep tissue phantom can thus be accomplished according to embodiments of the invention, by employing pulsed excitation to significant increase the QY. The pulsed excitation approach thereby greatly increase the applicability of UCNPs not only in diffuse optical imaging but also in many other biomedical applications, such as photodynamic therapy and remote activation of biomolecules in deep tissues. Further, metallic nanostructures may be effective in enhancing UC emissions owing to their local field enhancement effect by surface plasmonic coupling. Combining pulsed excitation and the decoration with metallic nanostructure may therefore allow a major scheme of using UCNPs in the diffuse light regime, due to the synergistic effect in increasing the excitation power-density. A method 100 according to an embodiment of the invention may thus comprise the step of providing 117 metallic nanostructures at said medium for exposure to said pulsed excitation light The pulsed excitation approach will also increase the applicability of migration-mediated UC emissions from ions such as Eu3+ and Tb3+ in biological applications, due to their high-order multi-stepwise excitation nature via excited Tm3+. In addition, this disclosure provides a general method for promoting the applications of nonlinear fluorophores (including UCNPs and triplet-triplet annihilation based upconverters) at low light conditions by increasing the excitation fluence rate through a limited illumination area.

The method 100 may thus comprise the step of exciting 104 the non-linear luminescent marker with a first pulse 201, i.e. the pulsed excitation light comprises at least one pulse of light, and further the step of detecting 106 luminescence from the luminescent marker due to said excitation light from said first pulse for providing single pulse luminescence molecular imaging from the first pulse. This single pulse imaging provides for several of the above described advantages over CW excitation.

The method 100 may comprise the step of matching 102 pulse characteristics of the at least one pulse, such as the length (w) of the pulse, with energy level transitions conditions of the non-linear luminescent marker to substantially provide for a desired population of energy levels of said non-linear luminescent marker related to emission of upconverted light so that said upconverted light is produced in a very efficient manner. The dynamics of the energy level transitions involved in the excitation/emission process is thereby taken into account to adapt the characteristics of the pulse. I.e. in order to provide for adequate and optimized intensity of the luminescence the pulse characteristics can be tailored to provide for the particular conditions by which population of the energy levels follows the desired scheme, e.g. by taking into account the duration of the lifetimes of the excited states that are involved in the emission process. The method 100 may thus comprise determining 116 a pulse width and/or a pulse waveform of said pulsed excitation light to provide excitation of said non-linear luminescent marker.

In this context, the method 100 may comprise the step of determining 104 a pulse length (w) of the pulsed excitation light to be in a range that provides excitation to the energy levels involved in the emission of upconverted light. The length of the pulse may be determined based on calculation of the lifetimes of the energy levels. The length of each pulse in a train of pulses may be in the range of about 1-100 ms. The system 600 may thus comprise a processing unit 603 operable to determine a pulse length of said excitation light based on calculation of energy level transitions conditions of said non-linear luminescent marker such as life time calculations.

The method 100 may comprise the step of determining 104 a pulse length (w) of the pulsed excitation light to be in the range of about 20-200 ms for single pulse luminescence molecular imaging, such as described in relation to FIG. 27*d*.

The method 100 may comprising determining 115 a dependence of the detected luminescence on the power of said excitation light for setting a predetermined characteristic of said pulsed excitation light.

Referring to FIG. 26*a*, signal gain may be obtained by using a pulse width as short as 0.8 ms. In addition, the optimal pulse width is material dependent. For instance, the optimal duration for Yb3+/Er3+ codoped materials would be shorter than that for Yb3+/Tm3+ codoped materials, as the intermediate energy states of Er3+ ions have usually short lifetimes than those of Tm3+ ions.

Having a pulse width of about 100 us will typically not provide sufficient signal gain.

A pulse length longer than the associated lifetimes may be advantageous in providing improved quantum yield and thereby improving the imaging capabilities. Gain may still be provided by having a pulse length of 0.8 ms while having lifetimes that are more than 0.8 ms. The gain by using pulsed excitation essentially originates from the higher peak power density. Too short pulse length will "eat" the benefit brought by the higher peak power density. When using 100 Hz, 50% duty cycle pulse, corresponding to 0.4 ms pulse width, there is no signal gain by using pulsed excitation for specific nanoparticles. Femtosecond or microsecond pulse laser to excite upconverting nanoparticles does not show signal gain as provided by the present disclosure. For the upper limit of the pulse width, the concern is that the detection system would wait too long time if the pulse length is large (since generally the duty cycle is small for this technique). For instance, for a pulsed excitation with a 100 ms pulse width and 10% duty cycle, the waiting time before collecting next-period luminescence signal generated by the laser is 900 ms. It is acceptable. But if it is even longer, it would not be economic in time in experiment.

For single pulse excitation it may be advantageous to increase the pulse length. The concern is that the laser will have a rest for quite some time after delivering the single pulse, so the luminescence signal will be generated only in such an interval. If the pulse duration is too short, the generated emission photons escaping from the surface of tissue would be too few to give a good signal (but QY increase is still there compared with equivalent CW excitation). A preferable interval of duration for single pulse could be 20-200 ms. If the single pulse is too long, it will too much like a CW source. In that case, it is not allowed to use preferably high peak power density according to ANSI standard.

Figure 20:
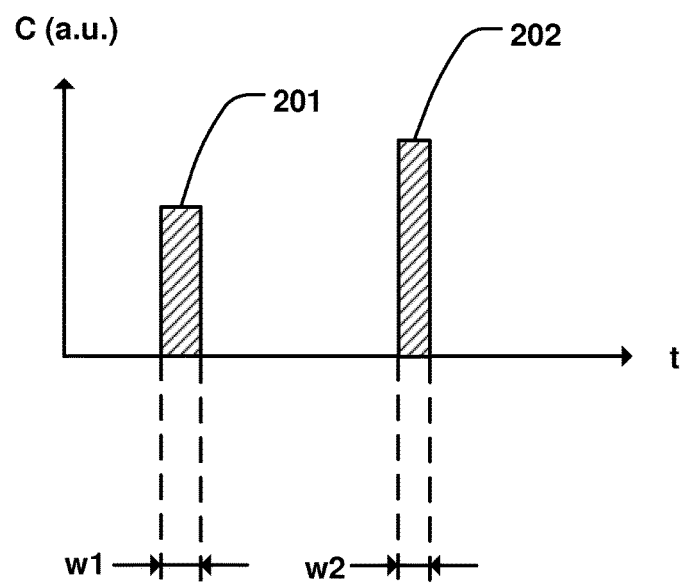
FIG. 20 illustrates excitation light comprising pulsed excitation light according to embodiments of the invention.
Figure 23:
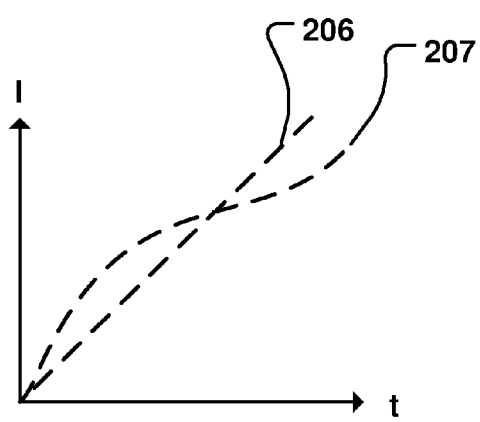
Figure 24:
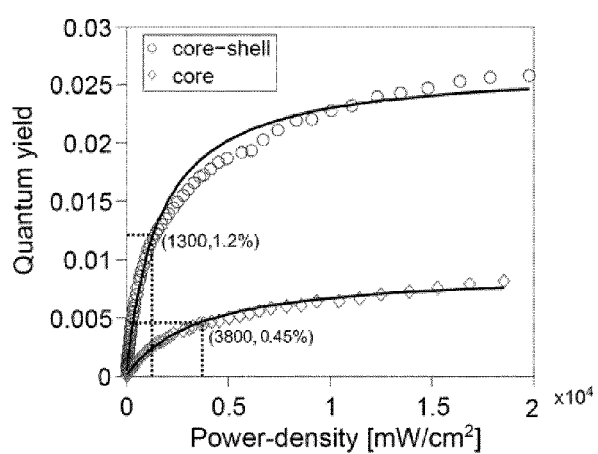
Figure 25:
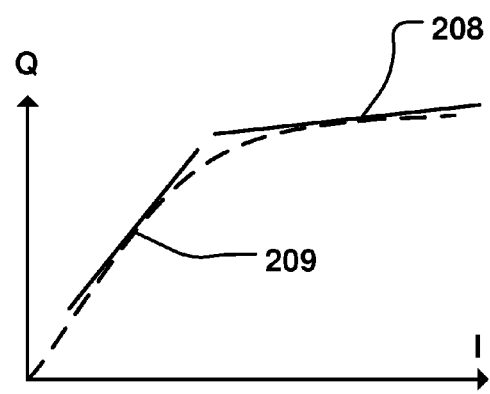

Reference is now made to FIGS. 22-25. The method 100 may comprise the step of varying 109 the power density (I) of the pulsed excitation light as a function of time (t) (as illustrated in FIG. 23 with reference to power density curves 206, 207), determining 110 a quantum yield dependence (Q/I) of the luminescence on said power density, and determining 111 a relative depth coordinate 203 of the marker position in the scattering medium based on the quantum yield dependence. A series of pulses (w1, w2), such as illustrated in FIG. 20 with different power densities may be used as excitation light. The quantum yield can be calculated for each of the pulses, and a dependence (Q/I) such as illustrated in FIG. 25 can be determined. Depending on how the quantum yield varies as the power density of the excitation light is varied, it is possible to determine if the marker is located relatively deep or shallow in the medium, as illustrated for markers 209 and 208 in FIG. 22 respectively. A marker 208 which has a more shallow position 204 in the medium will exhibit less variance in the luminescence quantum yield as the power density is varied, compared to a marker 209 which has a deeper position 205, as indicated in the Q/I curve in FIG. 25. The method 100 may comprise determining 112 the relative depth coordinate 203 based on a derivative (dQ/dI) of the quantum yield dependence. And the method 100 may accordingly comprise exciting 113 in sequence the non-linear luminescent marker with a first and second pulse 201, 202, having first and second power densities ($I_1$, $I_2$) respectively, and determining 114 the relative depth coordinate 203 based on a variation in the quantum yield from the first and second pulses. This allows for distinguishing between makers at different depths, without having to take into account the influence of their relative sizes. The system 600 may thus comprise a control unit 602 that is operable to vary the power density of the pulsed excitation light as a function of time (t), and a second processing unit 604 that is operable to determine a quantum yield dependence (Q/I) of the luminescence on the power density, and to determine a relative depth coordinate 203 of the marker position in the scattering medium based on said quantum yield dependence.

The system 600 may comprise a control unit 605 for performing the method 100 as described above. Further, use of a system 600 for performing the method 100 is provided according to the present disclosure. More particularly, the use of a system 600 is disclosed for luminescence imaging or luminescent tomography of tablets, and/or for diffuse optical imaging, and/or photodynamic therapy and/or remote activation of biomolecules in deep tissues, and/or single-shot deep tissue imaging, and/or for in-vivo or in-vitro luminescence imaging or luminescent tomography of a small animal, and/or for functional diagnostics, such as cancer diagnostics, by said luminescence imaging or luminescent tomography, and/or for superresolution microscopy comprising stimulated emission depletion (STED) or single-molecule detection using said non-linear luminescent marker as probe.

Potential Use of Pulsed Excitation in Upconverting Nanoparticles Based Photodynamic Therapy This proposed technique is a general approach for utilizing the upconversion capability more efficiently. It will work for not only Yb3+/Tm3+ codoped upconverting nanoparticles, but also for any upconverting nano- or bulk-materials. It works even better for high order upconversion emission, such as the blue and red emission of Tm3+ from three-photon processes. This approach is in particular useful in enhancing shorter wavelength upconversion emissions which are needed for upconverting nanoparticles based photodynamic therapy in biological tissue.

The present invention has been described above with reference to specific embodiments. However, other embodiments than the above described are equally possible within the scope of the invention. The different features and steps of the invention may be combined in other combinations than those described. The scope of the invention is only limited by the appended patent claims.

The method may be performed in-vivo at a living human or animal body. In this case, the markers may be preintroduced into the body in any manner, such as by injection into the blood stream or subcutaneously or directly into a tumour, or alternatively by topical application, pulmonary and other non-invasive methods. Such preintroduction can be performed separately from the remaining method. Such preintroduction can be performed in connection with the remaining method but shortly before.

Alternatively or additionally, the method may be performed at a human or animal body, which is sacrificed after the method is performed.

Alternatively or additionally, the method may be performed in vitro at a non-living human or animal body or part of a body, for example a brain-dead human or animal body.

Alternatively or additionally, the method may be performed at non-medical fields, such as filters or tablets.

Superresolution Microscopy Using UCNP as Probes

Superresolution microscopy has recently been developed and become a very interesting and useful tool for much biological research. There are two types of superresolution microscopy, one that relies on non-linear optical effects and one on single molecule detection. They both have in common that selected molecules provide a signal, while others are filtered out. The first category include stimulated emission depletion (STED) and saturated structured illumination microscopy (SSIM), while the single molecule detection comprises PALM (photoactivated localization microscopy), FPALM (fluorescence photoactivated localization microscopy) and STORM (stochastic optical reconstruction microscopy). The first category of superresolution microscopy utilize that probe can emit light, while nearby probes can be made non-emitting. The excited state will be depopulated for theses nearby probes. This procedure sets requirements for the probe used, one is that it has to be extremely photostable (as this is a non-linear effect requiring relatively high excitation power), non-blinking (as they should be active all the time while in the active state) and should have several energy levels that the probe can be light-switched to. UCNP could be an ideal probe for STED, with the unique properties, fulfilling these requirements.

The other category relies on that the probes can be photo-switched to other energy levels and become inactive. This is a single-molecule regime with low light levels. It could also rely on spontaneous photo-blinking. UCNP could become interesting probes for these techniques with the many energy levels in these probes.

The following references are incorporated by reference herein in their entirety for all purposes:
[Ref. 1] C. T. Xu, J. Axelsson, and S. Andersson-Engels, Appl. Phys. Lett. 94, 251107 (2009).
[Ref. 2] J. P. Culver, V. Ntziachristos, M. J. Holboke, and A. G. Yodh, Opt. Lett. 26, 701 (2001).
[Ref. 3] E. Alerstam, S. Andersson-Engels, and T. Svensson, J. Biomed. Opt. 13, 041304 (2008).

The invention claimed is:
1. A method of imaging a region in a scattering medium by diffuse luminescence molecular imaging, the method comprising:
providing at least one non-linear luminescent marker in said scattering medium at a marker position in said region;
exciting said non-linear luminescent marker by excitation light emitted by one or more light sources into an excitation volume from at least one light source position;
detecting luminescence from said luminescent marker due to said excitation light by a detector at a luminescent light detection position, and wherein said excitation light comprises pulsed excitation light; and
matching pulse characteristics of said at least one pulse with energy level transitions conditions of said non-linear luminescent marker to substantially provide for a desired population of energy levels of said non-linear luminescent marker related to emission of upconverted light so that said upconverted light is produced in an efficient manner.

2. The method of claim 1, wherein said pulsed excitation light comprises at least one pulse of light, and said method further comprises:
exciting said non-linear luminescent marker with a first pulse; and
detecting luminescence from said luminescent marker due to said excitation light from said first pulse for providing single pulse luminescence molecular imaging from said first pulse.

3. The method of claim 2, further comprising determining a pulse length of said pulsed excitation light to be in the range of about 20-200 ms for said single pulse luminescence molecular imaging.

4. The method of claim 1, further comprising determining a pulse length of said pulsed excitation light to be in the range of about 1-100 ms.

5. The method of claim 1, further comprising
varying the power density of said pulsed excitation light as a function of time,
determining a quantum yield dependence of the luminescence on said power density, and
determining a relative depth coordinate of said marker position in said scattering medium based on said quantum yield dependence.

6. The method of claim 5, further comprising determining said relative depth coordinate based on a derivative of said quantum yield dependence.

7. The method of claim 5, further comprising
exciting in sequence said non-linear luminescent marker with a first and second pulse having first and second power densities respectively, and
determining said relative depth coordinate based on a variation in said quantum yield from said first and second pulses.

8. The method of claim 1, further comprising determining a dependence of said detected luminescence on the power of said excitation light for setting a predetermined characteristic of said pulsed excitation light.

9. The method of claim 1, further comprising:
providing movement between said light source position and said marker position, and
imaging said luminescent marker based on a non-linear dependence of said detected luminescence on the excitation light intensity and said light source position in relation to said marker position, wherein said non-linear dependence is given by the relationship:

$$L=k*E^x,$$

wherein:
E is excitation light intensity in said excitation volume
L is luminescence light intensity from said luminescent marker
k is a positive constant, and
x is a positive number larger than one.

10. The method of claim 1, further comprising:
scanning said excitation light between a plurality of said light source positions such that said light source position is moved in relation to said marker position.

11. The method of claim 10, further comprising:
detecting said luminescence for each of said plurality of light source positions, said luminescence having a total luminescence intensity of said luminescent marker for each of said plurality of light source positions, and imaging said luminescent marker by making an image of said total luminescence intensity for each of said plurality of light source positions.

12. The method of claim 10, wherein said plurality of light source positions forms a grid pattern, said luminescence marker having a projected area on said grid pattern, wherein said projected area is less than the area covered by said grid pattern, and wherein said excitation volume is substantially localized to each of said plurality of light source positions such that said luminescent marker is partially excited if said light source position overlaps partially with said projected area.

13. The method of claim 1, further comprising:
exciting said luminescent marker by a first light source having a first wavelength from a first light source position, and
exciting said luminescent marker by a second light source having a second wavelength from a second light source position.

14. The method of claim 13, wherein said luminescent marker is excited by said first and second light sources simultaneously.

15. The method of claim 1, wherein said diffuse luminescent imaging comprises diffuse luminescent tomography, and/or power-scanning tomography using a single excitation point.

16. The method of claim 1, further comprising providing metallic nanostructures at said medium for exposure to said pulsed excitation light.

17. A method of imaging a region in a scattering medium by diffuse luminescence molecular imaging, the method comprising:
providing at least one non-linear luminescent marker in said scattering medium at a marker position in said region;
exciting said non-linear luminescent marker by excitation light emitted by one or more light sources into an excitation volume from at least one light source position; and
detecting luminescence from said luminescent marker due to said excitation light by a detector at a luminescent light detection position, and wherein said excitation light comprises pulsed excitation light; and
time-delaying the detection of the luminescence.

18. The method of claim 17, further comprising detecting said luminescence during a time interval succeeding a pulse of said excitation light.

19. A system for diffuse luminescence molecular imaging of a region of interest in a scattering medium, said system comprising a luminescent marker for use in said luminescent molecular imaging of said scattering medium, wherein said luminescent marker is a non-linear luminescent marker arranged in said scattering medium, said system comprising:
one or more light sources positioned by at least one light source position for exciting said luminescent marker by excitation light emitted by said one or more light sources into an excitation volume;
a detector at a luminescent light detection position detecting luminescence from said luminescent marker due to said excitation light, wherein said excitation light comprises pulsed excitation light; and
a processing unit configured to match pulse characteristics of said at least one pulse with energy level transitions conditions of said non-linear luminescent marker to substantially provide for a desired population of energy levels of said non-linear luminescent marker related to emission of upconverted light so that said upconverted light is produced in an efficient manner.

20. The system of claim 19, further comprising a detector unit that is operable to detect said luminescence during a time interval succeeding a pulse of said excitation light.

21. The system of claim 19, further comprising a processing unit operable to determine a pulse length of said excitation light based on calculation of energy level transitions conditions of said non-linear luminescent marker.

22. The system of claim 19, further comprising
a control unit operable to vary the power density of said pulsed excitation light as a function of time, and
a second processing unit operable to determine a quantum yield dependence of the luminescence on said power density, and to determine a relative depth coordinate of said marker position in said scattering medium based on said quantum yield dependence.

23. The system of claim 19, wherein said luminescent marker is a luminescent biological marker, and said scattering medium is tissue of a human or animal, said luminescent biological marker being arranged in said tissue.

24. The system of claim 19, wherein said luminescent marker comprises nanosized upconverting particles of sodium yttrium tetrafluoride ($NaYF_4$), co-doped with either $Yb^{3+}/Er^{3+}$ or $Yb^{3+}/Tm^{3+}$.

25. The system of claim 19, wherein said luminescent marker comprises nanosized upconverting particles comprising particles that are water soluble, and/or particles coated with a structure that is polar, and/or particles having hydroxyl groups attached the surfaces of the upconverting particles.

26. The system of claim 19, wherein said luminescent marker has a protective coating, and/or is biofunctionalized.

27. The system of claim 19, wherein said system is devised for luminescence molecular tomography.

28. The system of claim 19, wherein said non-linear markers are attached to an imaging contrast agent for an imaging modality different from a modality for said luminescent imaging.

29. The system of claim 19, wherein said non-linear marker is attached to an organic gadolinium complex or gadolinium compound, which has paramagnetic properties, and wherein said system further comprises a magnetic resonance imaging (MRI) apparatus for simultaneous imaging of said region of interest by MRI and luminescence molecular tomography.

30. The system of claim 19, wherein said excitation light is provided by a first light source having a first wavelength from a first light source position, and a second light source having a second wavelength from a second light source position.

31. The system of claim 30, wherein said excitation light is provided by said first and second light sources simultaneously.

32. A system for diffuse luminescence molecular imaging of a region of interest in a scattering medium, said system comprising a luminescent marker for use in said luminescent molecular imaging of said scattering medium, wherein said luminescent marker is a non-linear luminescent marker arranged in said scattering medium, said system comprising:
- one or more light sources positioned by at least one light source position for exciting said luminescent marker by excitation light emitted by said one or more light sources into an excitation volume;
- a detector at a luminescent light detection position detecting luminescence from said luminescent marker due to said excitation light, wherein said excitation light comprises pulsed excitation light; and
- a processing unit configured to time-delay the detection of the luminescence.

* * * * *